United States Patent

Heckmann et al.

[11] Patent Number: 6,143,774
[45] Date of Patent: *Nov. 7, 2000

[54] IMIDAZOLE N-BENZYLDIOXOL DERIVATIVES, METHOD FOR PREPARING SAME, RESULTING INTERMEDIATES, PHARMACEUTICAL COMPOSITIONS AND USE OF SAID DERIVATIVES AS ENDOTHELIN ANTAGONISTS

[75] Inventors: Bertrand Heckmann, Cachan; Simone Jouquey, Paris; Jean-Paul Vevert, Pantin; Jidong Zhang, Paris, all of France

[73] Assignee: Hoechst Marion Roussel, France

[ * ] Notice: This patent issued on a continued prosecution application filed under 37 CFR 1.53(d), and is subject to the twenty year patent term provisions of 35 U.S.C. 154(a)(2).

[21] Appl. No.: 09/068,630

[22] PCT Filed: Nov. 7, 1996

[86] PCT No.: PCT/FR96/01749

§ 371 Date: Jun. 9, 1998

§ 102(e) Date: Jun. 9, 1998

[87] PCT Pub. No.: WO97/17339

PCT Pub. Date: May 15, 1997

[30] Foreign Application Priority Data

Nov. 8, 1995 [FR] France ................................. 95 13189

[51] Int. Cl.[7] ...................... C07D 405/06; C07D 405/14; A61K 31/415
[52] U.S. Cl. ........................... 514/382; 514/397; 548/250; 548/252; 548/253; 548/311.7
[58] Field of Search ................................. 548/311.7, 250, 548/252, 253; 514/397, 382

[56] References Cited

U.S. PATENT DOCUMENTS 5,811,444  9/1998  Heckmann et al. ..................... 514/397
5,856,509  1/1999  Heckmann et al. ................. 548/311.1

FOREIGN PATENT DOCUMENTS

94/14434  7/1994  WIPO .
96/04276  2/1996  WIPO .

*Primary Examiner*—Fiona T. Power
*Attorney, Agent, or Firm*—Bierman, Muserlian and Lucas

[57] ABSTRACT

The invention relates to the new products of formula (I):

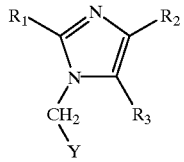

in which:

$R_1$ represents alkyl, optionally substituted or cycloalkyl optionally interrupted by heteroatoms, $R_2$; $R_3$ both represent or carry an acid function or an acid isosteric function, and Y represents phenyl substituted in particular by a dioxol radical, these products being in all the isomeric forms and the salts, as medicaments.

7 Claims, No Drawings

IMIDAZOLE N-BENZYLDIOXOL DERIVATIVES, METHOD FOR PREPARING SAME, RESULTING INTERMEDIATES, PHARMACEUTICAL COMPOSITIONS AND USE OF SAID DERIVATIVES AS ENDOTHELIN ANTAGONISTS

This application is a 371 of PCT FR96/01749 filed Nov. 7, 1996.

The present invention relates to new derivatives of imidazole N-benzyldioxole, their preparation process, the new intermediates obtained, their use as medicaments, the pharmaceutical compositions containing them and the new use of such derivatives of imidazole.

A subject of the present invention is the products of formula (I):

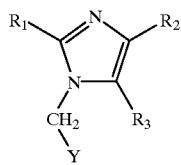

in which:
- $R_1$ represents an alkyl radical, optionally substituted by one or more hydroxyl or alkoxy radicals, the alkyl and alkoxy radicals being linear or branched and containing at most 6 carbon atoms, or a saturated or unsaturated cyclic radical constituted by 3 to 7 members, and optionally containing one or more identical or different heteroatoms chosen from oxygen, sulphur and nitrogen atoms,
- $R_2$ and $R_3$, identical or different, both represent or carry an acid function or an acid isosteric function and Y represents the phenyl radical substituted by a dioxol radical and optionally substituted by another substituent chosen from halogen atoms and alkoxy and alkyl radicals containing at most 4 carbon atoms,
- said products of formula (I) being in all possible racemic, enantiomeric and diastereoisomeric isomer forms, as well as the addition salts with mineral and organic acids or with mineral and organic bases of said products of formula (I).

In the products of formula (I) and in what follows:
- the term linear or branched alkyl radical designates the following radicals: methyl, ethyl, propyl, isopropyl, butyl, isobutyl, sec-butyl, tert-butyl, pentyl, isopentyl, hexyl, isohexyl and also heptyl, octyl, nonyl and decyl as well as their linear or branched position isomers,
- the term linear or branched alkoxy radical designates the following radicals: methoxy, ethoxy, propoxy, isopropoxy, linear, secondary or tertiary butoxy, pentoxy or hexoxy as well as their linear or branched position isomers,
- the term halogen atom preferably designates the chlorine atom, but can also represent a fluorine, bromine or iodine atom,
- the term saturated or unsaturated cyclic radical constituted by 3 to 7 members and optionally containing one or more identical or different heteroatoms, chosen from oxygen, sulphur or nitrogen atoms designates on the one hand a cycloalkyl radical such as for example the cyclopropyl, cyclobutyl radicals and quite particularly the cyclopentyl and cyclohexyl radicals or a carbocyclic radical interrupted by one or more heteroatoms chosen from oxygen, nitrogen or sulphur atoms such as quite particularly the dioxolane, dioxane, dithiolane, thiooxolane or thiooxane radical, on the other hand the phenyl, thienyl, furyl, pyridyl or tetrazolyl radicals, the term acid function or acid isosteric function designates the free, salified or esterified carboxy radical, the free or salified tetrazolyl radical, or the following radicals:

$SO_3H$, $-PO(OH)_2$,
$NHSO_2-CF_3$
$NH-SO_2-NH-V$
$NH-SO_2-NH-CO-V$
$NH-CO-V$
$NH-CO-NH-V$
$NH-CO-NH-SO_2-V$
$SO_2-NH-V$
$SO_2-NH-CO-V$
$SO_2-NH-CO-NH-V$
$CONH-V$
$CO-NH-OH$
$CONH-SO_2-V$ in which V represents a linear or branched alkyl or alkenyl radical containing at most 6 carbon atoms or a phenyl, pyridyl, pyrimidinyl, piperazinyl, thienyl or tetrazolyl radical, the alkyl, alkenyl and phenyl radicals being optionally substituted by one or more radicals chosen from halogen atoms and hydroxy, alkoxy or phenyl radicals, all the phenyl radicals and the piperazinyl radical being optionally substituted by a linear or branched alkyl radical containing at most 4 carbon atoms.

The carboxy radical or radicals of the products of formula (I) can be salified or esterified by various groups known to a man skilled in the art amongst which there can be mentioned, for example:
- among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine,
- among the esterification compounds, the alkyl radicals to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, hydroxyl, alkoxy, acyl, acyloxy, alkylthio, amino or aryl radicals such as, for example, in the following groups: chloromethyl, hydroxypropyl, methoxymethyl, propionyloxymethyl, methylthiomethyl, dimethylaminoethyl, benzyl or phenethyl.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, aryl-monosulphonic such as benzenesulphonic and aryldisulphonic.

It should be remembered that stereoisomerism can be defined in its broadest sense as the isomerism of compounds having the same developed formulae, but whose various groups are arranged differently in space, such as in particular in the boat and chair shapes of cyclohexane and monosubstituted cyclohexanes whose substituent can be in axial or equatorial position, and the different possible rotational conformations of ethane derivatives. However, another type of stereoisomerism exists, due to the different spatial arrangements of fixed substituents, either on double bonds, or on rings, which is often called geometrical isomerism or cis-trans isomerism. The term stereoisomeric is used in the present Application in its broadest sense and therefore relates to all of the compounds indicated above.

Therefore a subject of the present invention is the products of formula (I) as defined above in which: $R_1$ and Y have the meanings indicated above, and $R_2$ and $R_3$, identical or different, represent or carry a free, salified or esterified carboxy radical or a free or salified tetrazolyl radical, said products of formula (I) being in all possible racemic, enantiomeric and diastereoisomeric isomer forms, as well as the addition salts with mineral and organic acids or with mineral and organic bases of said products of formula (I).

A particular subject of the present invention is the products of formula (I) as defined above, in which: $R_1$ represents an alkyl radical, optionally substituted by one or more hydroxyl or alkoxy radicals, the alkyl and alkoxy radicals being linear or branched and containing at most 6 carbon atoms, a cycloalkyl radical containing 3 to 6 members and optionally containing one or two oxygen, nitrogen or sulphur atoms, a thienyl or furyl radical, $R_2$ represents a —$(CH_2)_n$—S—A radical, in which n represents an integer from 0 to 4, S represents a sulphur atom and A represents:

either a linear or branched alkyl radical, containing at most 10 carbon atoms and substituted by a free, salified or esterified carboxy radical or by a free or salified tetrazolyl radical, or a cycloalkyl radical constituted by 5 or 6 members, optionally containing one or two oxygen or nitrogen atoms and substituted by a free, salified or esterified carboxy radical, by a free or salified tetrazolyl radical, or by a linear or branched alkyl, alkenyl, alkoxy or alkylthio radical containing at most 6 carbon atoms optionally interrupted by an oxygen or sulphur atom, and themselves substituted by a free, salified or esterified carboxy radical or by a free or salified tetrazolyl radical, $R_3$ represents a free, salified or esterified carboxy radical or a free or salified tetarazolyl radical, and Y has the meaning indicated above, said products of formula (I) being in all possible racemic, enantiomeric and diastereoisomeric isomer forms, as well as the addition salts with mineral and organic acids or with mineral and organic bases of said products of formula (I).

In the products of formula (I) and in what follows:

the term linear or branched alkenyl radical designates vinyl, allyl, 1-propenyl, butenyl, 1-butenyl, pentenyl or hexenyl radicals as well as their linear or branched position isomers, the term alkylthio radical designates radicals in which the alkyl radical is as defined above such as for example in methylthio, ethylthio, propylthio, isopropylthio, butylthio, sec-butylthio, tert-butylthio, isopentylthio, isohexylthio, but also heptylthio, octylthio, nonylthio or decylthio as well as their linear or branched position isomers.

Among the alkyl, alkenyl, alkoxy or alkylthio radicals interrupted by one or more heteroatoms, there can be mentioned for example the following radicals: methoxymethyl, methoxyethoxymethyl, propylthiopropyl, propyloxypropyl, propylthioethyl, methylthiomethyl, as well as these same radicals in which the alkyl radicals such as methyl, ethyl or propyl are replaced by alkenyl, alkoxy or alkylthio radicals as defined above to give for example the following radicals: methoxyvinyl, methoxyallyl, methoxymethoxy, methoxyethoxy, methoxymethylthio, methoxyethylthio, ethoxypropylthio, ethylthiopropoxy, propylthiomethoxy or also ethylthioethoxy.

A more particular subject of the present invention is the products of formula (I) as defined above, in which $R_1$, represents one of the following radicals: methoxymethyl, ethyl, n-propyl, isopropyl, n-butyl, isobutyl, terbutyl, cyclopentyl, cyclohexyl, dioxolane, dioxane, dithiolane, thienyl or furyl, $R_2$ represents either an alkylthio radical containing 3 to 10 carbon atoms substituted by a free, salified or esterified carboxy radical or by a free or salified tetrazolyl radical, or a cyclohexylthio, cyclopentylthio or piperidinylthio radical substituted by a free, salified or esterified carboxy radical; by a free or salified tetrazolyl radical; or by an alkyl, alkenyl, alkoxy or alkylthio radical containing at most 4 carbon atoms themselves substituted by a free, salified or esterified carboxy radical or by a free or salified tetrazolyl radical, $R_3$ represents a free, salified or esterified carboxy radical or a free or salified tetrazolyl radical, and Y represents a phenyl radical substituted by a dioxol radical and optionally substituted by a halogen atom, said products of formula (I) being in all possible racemic, enantiomeric and diastereoisomeric isomer forms, as well as the addition salts with mineral and organic acids or with mineral and organic bases of said products of formula (I).

An even more particular subject of the invention is the products of formula (I) as defined above, in which $R_1$ represents a methoxymethyl, n-propyl, isopropyl, n-butyl, isobutyl, terbutyl and dioxolane radical, $R_2$ represents either a linear or branched alkylthio radical containing 3, 4 or 5 carbon atoms, substituted by a free, salified or esterified carboxy radical or the cyclohexylthio radical substituted by a free, salified or esterified carboxy radical, or by an alkyl or alkenyl radical containing at most 4 carbon atoms, themselves substituted by a free, salified or esterified carboxy radical, $R_3$ represents a free, esterified or salified carboxy radical, Y represents a phenyl radical substituted by a dioxol radical and by a halogen atom, said products of formula (I) being in all possible racemic, enantiomeric and diastereoisomeric isomer forms, as well as the addition salts with mineral and organic acids or with mineral and organic bases of said products of formula (I).

A quite particular subject of the present invention is the products of formula (I) as defined above, corresponding to the following formulae:

4-((4-(carboxymethylene) cyclohexyl) thio)-1-((6-chloro-1,3-benzodioxol-5-yl) methyl)-2-propyl-1H-imidazole-5-carboxylic acid, 4-((5-carboxypentyl) thio)-1-((6-chloro-1,3-benzodioxol-5-yl) methyl)-2-(1,3-dioxolan-2-yl)-1H-imidazole-5-carboxylic acid, 4-((4-(carboxymethyl) cyclohexyl) thio)-1-((6-chloro-1,3-benzodioxol-5-yl) methyl)-2-propyl-1H-imidazole-5-carboxylic acid, 1-((6-chloro 1,3-benzodioxol-5-yl) methyl) 4-((4-carboxy-cyclohexyl) thio) 2-propyl 1H-imidazole 5-carboxylic acid, 4-(((4-carboxycyclohexyl) methyl) thio) 1-((6-chloro 1,3-benzodioxol-5-yl) methyl) 2-propyl 1H-imidazole 5-carboxylic acid, cis 4-(((2-((carboxymethoxy) methyl) cyclohexyl) methyl) thio) 1-((6-chloro 1,3-benzodioxol-5-yl) methyl) 2-propyl 1H-imidazole 5-carboxylic acid, trans 4-((4-(carboxymethyl) cyclohexyl) thio) 1-((6-chloro 1,3-benzodioxol-5-yl) methyl) 2-(1,3-dioxolan-2-yl) 1H-imidazole 5-carboxylic acid, 4-((4-(carboxymethyl) cyclohexyl) thio) 1-((6-chloro 1,3-benzodioxol-5-yl) methyl) 2-(2-furanyl) 1H-imidazole 5-carboxylic acid, trans 4-((4-(carboxymethyl) cyclohexyl) thio) 1-((6-chloro 1,3-benzodioxol-5-yl) methyl) 2-cyclopentyl 1H-imidazole 5-carboxylic acid, trans 3-((4-(carboxymethyl) cyclohexyl) thio) 1-((6-chloro 1,3-benzodioxol-5-yl) methyl) 2-(2-thienyl) 1H-imidazole 5-carboxylic acid, 4-((4-carboxycyclohexyl) thio) 1-((6-chloro 1,3-benzodioxol-5-yl) methyl) 2-(2-furanyl) 1H-imidazole 5-carboxylic acid, disodium salt of 4-((4-(carboxymethyl) cyclohexyl) thio) 1-((6-chloro 1,3-benzodioxol-5-yl) methyl) 2-propyl 1H-imidazole 5-carboxylic acid, dipotassium salt of 4-((4-(carboxymethyl) cyclohexyl) thio) 1-((6-chloro 1,3-benzodioxol-5-yl) methyl) 2-propyl 1H-imidazole 5-carboxylic acid.

Also a subject of the present invention is the preparation process for the products of formula (I), as defined above, characterized in that: either a compound of formula (II):

(II)

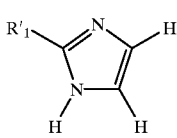

in which $R'_1$ has the meaning indicated above for $R_1$, in which the optional reactive functions are optionally protected by protective groups, is subjected to a reaction with a compound of formula (III):

(III)

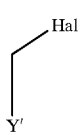

in which Hal represents a halogen atom, and Y' has the meaning indicated above for Y, in which the optional reactive functions are optionally protected by protective groups, in order to obtain the product of formula (IV):

(IV)

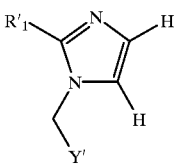

in which $R'_1$ and Y' have the meanings indicated above, which product of formula (IV) can be subjected to a halogenation reaction, in order to obtain the product of formula (V):

(V)

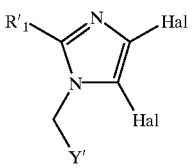

in which $R'_1$, Hal and Y' have the meanings indicated above, or a compound of formula (VI):

(VI)

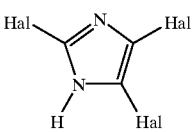

in which Hal has the meaning indicated above, is subjected either to a reaction with the compound of formula (III) as defined above, or to the action of a protective group P, in order to obtain a product of formula (VII):

(VII)

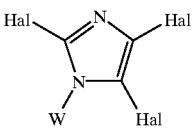

in which Hal has the meaning indicated above and W represents either —CH$_2$—Y' with Y' as defined above, or P which represents a protective group of the nitrogen atom, which product of formula (VII) is subjected to a halogen-metal exchange reaction then to a reaction with dimethylformamide or with an electrophile of formula (VIII$_a$) or (VIII$_b$):

$$L_1L-CHO \quad (VIII_a)$$

$$L_1-CO-Cl \quad (VIII_b)$$

in which $L_1$ represents a linear or branched alkyl radical containing at most 6 carbon atoms and optionally substituted by a protected alkoxyl or hydroxy radical, in order to obtain a product of formula (IX):

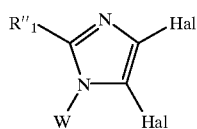 (IX)

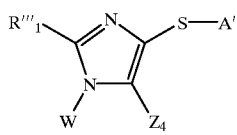 (XIV)

in which Hal and W have the meanings indicated above, R'''$_1$ represents an alkyl-carbonyl, formyl or hydroxyalkyl radical in which the alkyl radical has the meaning indicated above and in which the optional reactive functions are optionally protected by protective groups, which products of formulae (V) and (IX) can be subjected to a halogen-metal exchange reaction on one of the halogen atoms then to a reaction with $CO_2$ or DMF or an electrophilic compound of formula (X):

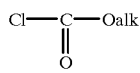 (X)

in which alk represents an alkyl radical containing at most 4 carbon atoms, in order to obtain the compound of formula (XI):

in which R'''$_1$, A' and W have the meanings indicated above, and $Z_4$ represents the cyano radical or the carboxy radical free or esterified by a linear or branched alkyl radical containing at most 6 carbon atoms, which products of formula (XIII) or (XIV), in the case where W represents P as defined above and after release of the amine function blocked by P as defined above, are reacted with the compound of formula (III) as defined above, in order to obtain a product of formula (XV):

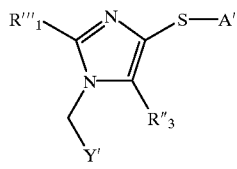 (XV)

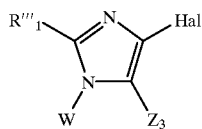 (XI)

in which R'''$_1$ represents R'$_1$ or R''$_1$ as defined above, Hal and W have the meanings indicated above and $Z_3$ represents the free or esterified carboxy radical or the formyl radical, which compound of formula (XI) can be subjected to a reaction with a compound of formula (XII):

A'—S—M (XII)

in which S represents a sulphur atom, M represents a metal such as sodium, potassium or copper and A' represents A as defined above, in which the optional reactive functions are optionally protected by protective groups in order to obtain the compound of formula (XIII):

in which R'''$_1$, A' and Y' have the meanings indicated above, and R''$_3$ represents $Z_3$ or $Z_4$ as defined above, or a compound of formula (XVI):

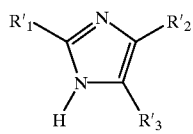 (XVI)

in which R'$_1$ has the meaning indicated above and R'$_2$ and R'$_3$ have the meanings indicated above for $R_2$ and $R_3$ respectively in which the optional reactive functions are optionally protected by protective groups, is subjected to a reaction with the compound of formula (III) as defined above, in order to obtain a product of formula ($I_1$):

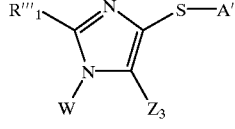 (XIII)

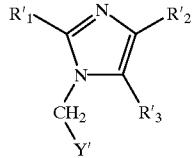 ($I_1$)

in which R'''$_1$, Y', A', $Z_3$ and W have the meanings indicated above, which product of formula (XIII) when $Z_3$ represents the formyl radical, can be subjected to an oxidation reaction in order to obtain the product of formula (XIV):

in which R'$_1$, R'$_2$, R'$_3$ and Y' have the definitions indicated above, or a compound of formula (XVII):

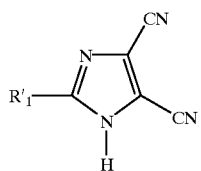
(XVII)

in which $R'_1$ has the meaning indicated previously, is subjected to a hydrolysis reaction in order to obtain the product of formula (XVIII):

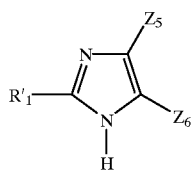
(XVIII)

in which $R'_1$ has the meaning indicated previously and one or both of $Z_5$ and $Z_6$ represents a free or esterified carboxy radical and if appropriate, the other one of $Z_5$ and $Z_6$ retaining the CN value, which product of formula (XVIII) is reacted with the compound of formula (III) as defined above in order to obtain the product of formula (XIX):

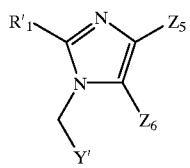
(XIX)

in which $R'_1$, Y', $Z_5$ and $Z_6$ have the meanings indicated previously, or a compound of formula (XX):

 (XX)

in which Y' has the meaning indicated above, is subjected to a compound of formula (XXI):

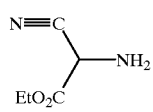
(XXI)

in order to obtain, after reduction of the intermediate imine, a product of formula (XXII):

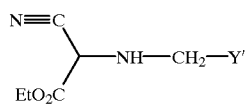
(XXII)

in which Y' has the meaning indicated above, which is subjected to a compound of formula (XXIII):

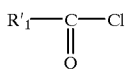
(XXIII)

in which $R'_1$ has the meaning indicated above, in order to obtain the product of formula (XXIV):

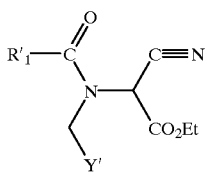
(XXIV)

in which Y' and $R'_1$ have the meanings indicated above, which is subjected to a compound of formula (XXV):

A'—S—H (XXV)

in which A' has the meaning indicated above, in order to obtain the product of formula (XXVI):

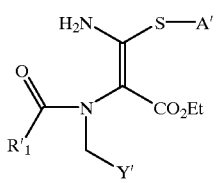
(XXVI)

in which Y', $R'_1$ and A' have the meanings indicated above, which is cyclized into the product of formula ($I_2$):

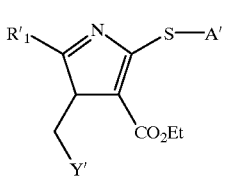
($I_2$)

in which Y', $R'_1$ and A' have the meanings indicated above, or a compound of formula (XXI):

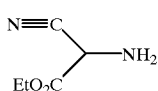
(XXI)

is subjected to the action of a compound of formula (XXIII):

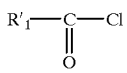
(XXIII)

in which $R'_1$ has the meaning indicated above in order to obtain a compound of formula (XXIVa):

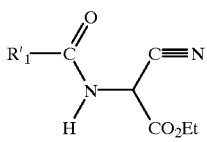

(XXIVa)

in which R'₁, has the meaning indicated above, which is subjected to the action of a compound of formula (XXV):

 (XXV)

in which A' has the meaning indicated above in order to obtain a product of formula (XXVIa):

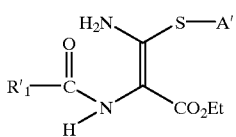

(XXVIa)

in which R'₁ and A' have the meanings indicated previously, which is cyclized into the product of formula (XXVIb):

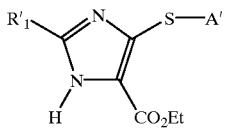

(XXVIb)

in which R' and A' have the meaning indicated previously, which is subjected to the action of a product of formula (III):

(III)

in which Hal and Y' have the meaning indicated above in order to obtain a product of formula (I₂) as defined above, which products of formulae (IX), (XI), (XIII), (XIV), (XV), (XIX), (I₁) and (I₂) can be products of formula (I) and which, in order to obtain products or other products of formula (I), can be subjected, if desired and if necessary, to one or more of the following conversion reactions, in any order:

a) an esterification reaction of the acid function, b) a saponification reaction of the ester function into an acid function, c) a conversion reaction of the ester function into a formyl function, d) a conversion reaction of the cyano function into an acid function, e) an oxidation reaction of the alkylthio group into a corresponding sulphoxide or sulphone, f) a reduction reaction of the free or esterified carboxy function to an alcohol function, g) a conversion reaction of the alkoxy function into a hydroxyl function, or also of the hydroxyl function into an alkoxy function, h) an oxidation reaction of the alcohol function into an aldehyde, acid or ketone function, i) a conversion reaction of the formyl radical into a carbamoyl radical, j) a conversion reaction of the carbamoyl radical into a nitrile radical, k) a conversion reaction of the nitrile radical into a tetrazolyl radical, l) a conversion reaction of a halogenated function into a formyl or esterified carboxy function, m) a conversion reaction of a formyl radical into a CH₂—CO₂alk or CH=CH—CO₂alk function in which alk represents an alkyl radical containing 1 to 4 carbon atoms, then if appropriate, conversion into the corresponding acid, n) a conversion reaction of a formyl radical into a —CH=CH—A' radical then if appropriate into a —CH₂—CH₂A' radical, o) an oxidation reaction of the S-alk radical into

S-alk then conversion into an SH function and if appropriate into S-A' in which alk and A' have the meaning indicated previously, p) a reaction to eliminate the protective groups which can be carried by the protected reactive functions, q) a salification reaction by a mineral or organic acid or by a base in order to obtain the corresponding salt, r) a resolution reaction of the racemic forms into resolved products, said products of formula (I) thus obtained being in all possible racemic, enantiomeric and diastereoisomeric isomer forms.

It can be noted that such conversion reactions of substituents into other substituents can also be carried out on the starting products as well as on the intermediate products as defined above before continuing the synthesis according to the reactions indicated in the process described above.

Under preferred conditions for implementing the invention, the process described above can be carried out in the following manner:

In the product of formula (III), the halogen atom preferably represents a bromine atom but can also represent a chlorine or iodine atom. The condensation reaction of the imidazoles of formulae (II), (VI), (XVI), (XIII) and (XIV) as defined above (in the case of the products of formulae (XIII) and (XIV), when w represents P and after deprotection of the nitrogen atom), with the compound of formula (III) as defined above, in order to obtain respectively the products of formulae (IV), (VII) when W represents Y', (XV) and (I₁) as defined above, can be carried out in a solvent such as for example dimethylformamide or also dimethylacetamide, tetrahydrofuran, dimethoxyethane or dimethylsulphoxide under reflux of the solvent or at ambient temperature, preferably under agitation; the reaction is preferably carried out in the presence of a base such as for example sodium or potassium hydride or also sodium or potassium carbonate, sodium or potassium methylate or ethylate or tert-butylate.

The halogenation reaction of the compound of formula (IV) as defined above into a compound of formula (V) as defined above, can be carried out under the usual conditions known to a man skilled in the art and in particular by bromination using NBS in $CH_2Cl_2$ or also $Br_2$ in acetic acid.

The compounds of formulae (V), (VII) and (IX) as defined above can be subjected to a halogen-metal exchange reaction on the halogen atom by reaction with an organometallic compound such as nBuli or ethyl magnesium bromide in a solvent such as tetrahydrofuran at a temperature of approximately $-78°$ C. for Buli and ambient temperature for ethyl magnesium bromide.

The carboxylation reaction using $CO_2$ and the formylation reaction using dimethylformamide of the compounds of formulae (V) or (IX) into the compound of formula (XI) can be carried out according to the usual conditions known to a man skilled in the art namely for example in tetrahydrofuran at ambient temperature.

$L_1$ represents an alkyl radical such that $R_1"$ represents the corresponding values chosen from values of $R_1$ as defined above in which the optional reactive functions are optionally protected by protective groups.

The reaction of the compound of formula (V) or (IX) as defined above with the compound of formula (X), as defined above, in order to obtain the corresponding compound of respective formula (XI) as defined above can be carried out in an identical manner by using ethyl magnesium bromide as metallation agent in tetrahydrofuran at ambient temperature.

The reaction of the compound of formula (VII) with the compounds of formula $(VIII_a)$ or $(VIII_b)$ can be carried out according to the usual conditions known to a man skilled in the art namely for example in tetrahydrofuran at ambient temperature.

The amine function of the compounds of formulae (XIII) and (XIV) as defined above, protected by P as defined above, can be released under the usual conditions known to a man skilled in the art and in particular when P represents the $-CH_2-O-(CH_2)_2-Si(CH_3)_3$ radical, the hydrogen atom can be released in trifluoroacetic acid or also in the presence of a fluoride ion.

The saponification reaction can be carried out according to the usual methods known to a man skilled in the art, such as for example in a solvent such as methanol or ethanol, dioxane or dimethoxyethane, in the presence of soda or potash or also caesium carbonate.

The reduction or oxidation reactions of the product of formula (XIII) into the product of formula (XIV) can be carried out according to the usual methods known to a man skilled in the art.

In the reactions described above, the operation can be carried out in the following manner:

the reaction of the compound of formula (XX) with the compound of formula (XXI) to obtain the compound of formula (XXII) can be carried out in a solvent such as for example methylene chloride in the presence of an acid catalyst such as for example amberlist then by reduction for example with sodium borohydride in acetic acid and methylene chloride, the reaction of the compound of formula (XXII) or (XXI) with the compound of formula (XXIII) to obtain respectively the compound of formula (XXIV) or (XXIVa) can be carried out in a solvent such as for example tetrahydrofuran or methylene chloride, in the presence of a base such as pyridine or also triethylamine or sodium or potassium carbonate, the reaction of the compound of formula (XXIV) or (XXIVa) with the compound of formula (XXV) to obtain respectively the compound of formula (XXVI) or (XXVIa) can be carried out in an alcohol such as methanol or ethanol in the presence of a base such as triethylamine or pyridine.

the cyclization of the compound of formula (XXVI) or $(XXVI_a)$ respectively into the product of formula $(I_2)$ or $(XXVI_b)$ can be carried out in the presence of an anhydride such as for example propane phosphonic anhydride in ethyl acetate.

the reaction of the compound of formula (XXVIa) with the compound of formula (III) can be carried out in an identical manner to that indicated above for the condensation reaction of the product of formula (III) and the imidazoles of formulae (II), (VI), (XVI), (XIII) and (XIV).

According to the values of $R'_1, R"_1, R'''_1, R'_2, R'_3, R"_3$, the products of formulae (IX), (XI), (XIII), (XIV), (XV), (XIX), $(I_1)$ and $(I_2)$ constitute or do not constitute products of formula (I) and can give products of formula (I), or be converted into other products of formula (I) by being subjected to one or more of reactions a) to r) indicated above.

Thus the various reactive functions which can be carried by some of the compounds of the reactions defined above can, if necessary, be protected: they are for example the hydroxyl, acyl, free carboxy radicals or also the amino and monoalkylamino radicals which can be protected by the appropriate protective groups.

The following non-exhaustive list of examples of the protection of the reactive functions can be mentioned:

the hydroxyl groups can be protected for example by alkyl radicals such as tert-butyl, trimethylsilyl, tert-butyldimethylsilyl, methoxymethyl, tetrahydropyrannyl, benzyl or acetyl, the amino groups can be protected for example by acetyl, trityl, benzyl, tert-butoxycarbonyl, phthalimido radicals or other radicals known in the chemistry of the peptides, the acyl groups such as the formyl group can be protected for example in the form of cyclic or non-cyclic ketals or thioketals such as dimethyl or diethylketal or ethylene dioxyketal, or diethylthioketal or ethylenedithioketal, the acid functions of the products described above can be, if desired, amidified by a primary or secondary amine for example in methylene chloride in the presence, for example, of 1-ethyl-3-(dimethylaminopropyl) carbodiimide hydrochloride at ambient temperature:

the acid functions can be protected for example in the form of esters formed with easily cleavable esters such as benzyl or terbutyl esters or esters known in the chemistry of the peptides.

The reactions to which the products of formulae (IX), (XI), (XIII), (XIV), (XV), (XIX), $(I_1)$ and $(I_2)$ as defined above can be subjected, if desired or if necessary, can be carried out, for example, as indicated hereafter:

a) The products described above can, if desired, be subjected to esterification reactions on the optional carboxy functions, which can be carried out according to the usual methods known to a man skilled in the art.

b) The optional conversions of the ester functions into an acid function of the products described above can be, if desired, carried out under the usual conditions known to a man skilled in the art in particular by acid or alkaline hydrolysis for example by soda or potash in an alcoholic medium such as, for example, in methanol or also by hydrochloric or sulphuric acid.

c) The conversion reaction of the ester function

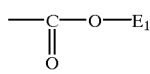

in which $E_1$ can represent an optionally substituted and optionally protected alkyl radical, into a formyl radical can be carried out as is described in the experimental part, or according to the usual methods known to a man skilled in the art, in particular by saponification of the ester into an acid, then converted into the acid chloride for example by the action of thionyl chloride, and then reduced for example by hydrogenation on palladium.

d) The optional cyano functions of the products described above can be, if desired, converted into an acid function under the usual conditions known to a man skilled in the art for example by a double hydrolysis carried out in an acid medium such as for example in a sulphuric acid, glacial acetic acid and water mixture, these three compounds preferably being in equal proportions, or also in a soda, ethanol and water mixture under reflux.

e) The optional alkylthio groups of the products described above can be, if desired, converted into the corresponding sulphoxide or sulphone functions under the usual conditions known to a man skilled in the art such as for example by peracids such as for example peracetic acid or metachloro-perbenzoic acid or also by ozone, oxone, sodium periodate in a solvent such as for example methylene chloride or dioxane at ambient temperature.

The obtaining of the sulphoxide function can be encouraged by an equimolar mixture of the product containing an alkylthio group and a reagent such as in particular a peracid.

The obtaining of the sulphone function can be encouraged by a mixture of the product containing an alkylthio group with an excess of reagent such as in particular a peracid.

f) The optional free or esterified carboxy functions of the products described above can be, if desired, reduced to an alcohol function by the methods known to a man skilled in the art: the optional esterified carboxy functions can be, if desired, reduced to an alcohol function by the methods known to a man skilled in the art and in particular by lithium and aluminium hydride in a solvent such as for example tetrahydrofuran or also dioxane or ethyl ether.

The optional free carboxy functions of the products described above can be, if desired, reduced to an alcohol function in particular by boron hydride.

g) The optional alkoxy functions such as in particular methoxy of the products described above can be, if desired, converted into a hydroxyl function under the usual conditions known to a man skilled in the art for example by boron tribromide in a solvent such as for example methylene chloride, by pyridine hydrobromide or hydrochloride or also by hydrobromic of hydrochloric acid in water or trifluoroacetic acid under reflux.

h) The optional alcohol functions of the products described above can be, if desired, converted into an aldehyde or acid function by oxidation under the usual conditions known to a man skilled in the art such as for example by the action of manganese oxide in order to obtain aldehydes or of Jones reagent in order to produce acids.

i) j) The conversion reactions of the formyl radical into a carbamoyl radical and of the carbamoyl radical into a nitrile radical, are in particular carried out for $R_3$ and $R_4$ according to the usual conditions known to a man skilled in the art, such as for example passage via the keto nitrile and displacement by an amine (Chem. Comm. 1971, p.733).

k) The optional nitrile functions of the products described above can be, if desired, converted into tetrazolyl under the usual conditions known to a man skilled in the art such as for example by the cycloaddition of a metal azide such as for example sodium azide or a trialkyltin azide on the nitrile function as indicated in the method described in the article referenced as follows:

J. Organometallic Chemistry., 33, 337 (1971) KOZIMA S. et al.

It can be noted that the conversion reaction of a carbamate into urea and in particular of a sulphonylcarbamate into sulphonylurea, can be carried out for example under reflux of a solvent such as for example toluene in the presence of the appropriate amine.

l) The conversion of a halogenated radical into a formyl radical can in particular be carried out by the action of an organo-metallic derivative, for example ethyl magnesium bromide, in an organic solvent, m) the conversion of the formyl radical into a CH=CH—$CO_2$alk radical can be carried out by a Wittig-type reaction by condensation of an appropriate phosphonium salt in the presence of sodium hydride; the conversion into an acid is carried out by hydrolysis, for example using a base such as soda in an alcoholic medium, n) the conversion of the formyl radical into a —CH=CH—A' radical can be carried out by a Wittig reaction as indicated above; the conversion into the —$CH_2$—$CH_2$—A' radical is carried out by reduction, using hydrogen in the presence of a catalyst, for example platinum oxide.

It can be noted that the conversion of the formyl radical into a $CH_2OH$ radical can be carried out using a reducing agent, for example sodium borohydride in ethanol at ambient temperature; the conversion into the —$CH_2$—SR radical can be carried out by the action of the appropriate R-SH thiol on the intermediate mesylate prepared beforehand by the action of mesyl chloride on alcohol in the presence of Hunig base, o) the oxidation of the S-alk substituent into the sulphoxide can be carried out for example, by the action of metachloroperbenzoic acid; the conversion of the thiol is obtained by the PUMMERER reaction for example in the presence of trifluoroacetic anhydride; the conversion of the SH substituent into $SZ_2$ can be obtained by the action of a halogenated derivative $Hal-Z_2$ for example iodocyclohexane.

It is understood that the reactions described above can be carried out according to the usual methods known to a man skilled in the art.

p) The elimination of the protective groups such as for example those indicated above can be carried out under the usual conditions known to a man skilled in the art in particular by an acid hydrolysis carried out with an acid such as hydrochloric, benzene sulphonic or paratoluene sulphonic, formic or trifluoroacetic acid or also by catalytic hydrogenation.

The phthalimido group can be eliminated by hydrazine.

A list of the different protective group which can be used will be found for example in the Patent BF 2,499,995.

q) The products described above can, if desired, be subjected to salification reactions for example by a mineral or organic acid or by a mineral or organic base according to the usual methods known to a man skilled in the art.

r) The optional optically-active forms of the products described above can be prepared by resolution of the racemics according to the usual methods known to a man skilled in the art.

Illustrations of such reactions defined above are given in the preparation of the examples described hereafter.

The compounds of formula (I) as defined above as well as their addition salts with acids have useful pharmacological properties.

The products of formula (I) as defined above, are endowed with antagonistic properties for the endothelin receptors and are thus in particular inhibitors of the effects of endothelin, in particular the vaso-constrictive and hypertensive effects induced by endothelin. In particular an anti-ischemic effect can be noted, the vasoconstrictive activity of endothelin being eliminated.

The products of formula (I) are also capable of opposing the stimulating effects of endothelin at the level of all cell types, in particular smooth muscle cells, fibroblasts, neuronal cells and bone cells.

These properties justify their use in therapeutics and a particular subject of the invention is as medicaments, the products of formula (I), said products of formula (I) being in all possible racemic, enantiomeric and diastereoisomeric isomer forms, as well as the addition salts with pharmaceutically acceptable mineral and organic acids or mineral and organic bases of said products of formula (I).

Therefore a more particular subject of the invention is as medicaments, the products as defined by formula (I) above, in which $R_1$ represents a methoxymethyl, ethyl, n-propyl, isopropyl, n-butyl, isobutyl, terbutyl, cyclopentyl, cyclohexyl, dioxolane, dioxane, dithiolane, thienyl or furyl radical, $R_2$ represents either an alkylthio radical containing 3 to 10 carbon atoms substituted by a free, salified or esterified carboxy radical or by a free or salified tetrazolyl radical, or a cyclohexylthio, cyclopentylthio or piperidinylthio radical substituted by a free, salified or esterified carboxy radical; by a free or salified tetrazolyl radical; or by an alkyl, alkenyl, alkoxy or alkylthio radical containing at most 4 carbon atoms themselves substituted by a free, salified or esterified carboxy radical or by a free or salified tetrazolyl radical, $R_3$ represents a free, salified or esterified carboxy radical or a free or salified tetrazolyl radical, and Y represents a phenyl radical substituted by a dioxol radical and optionally substituted by a halogen atom, said products of formula (I) being in all possible racemic or ptically active isomer forms, as well as the addition salts with pharmaceutically acceptable mineral and organic acids or mineral and organic bases of said products of formula (I). A quite particular subject of the invention is, as medicaments, the products described hereafter in the examples and in particular the products of formula (I) as defined above, corresponding to the following formulae:

4-((4-(carboxymethylene) cyclohexyl) thio)-1-((6-chloro-1,3-benzodioxol-5-yl) methyl)-2-propyl-1H-imidazole-5-carboxylic acid, 4-((5-carboxypentyl) thio)-1-((6-chloro-1,3-benzodioxol-5-yl) methyl)-2-(1,3-dioxolan-2-yl)-1H-imidazole-5-carboxylic acid, 4-((4-(carboxymethyl) cyclohexyl) thio)-1-((6-chloro-1,3-benzodioxol-5-yl) methyl)-2-propyl-1H-imidazole-5-carboxylic acid, 1-((6-chloro 1,3-benzodioxol-5-yl) methyl) 4-((4-carboxycyclohexyl) thio) 2-propyl 1H-imidazole 5-carboxylic acid, 4-(((4-carboxycyclohexyl) methyl) thio) 1-((6-chloro 1,3-benzodioxol-5-yl) methyl) 2-propyl 1H-imidazole 5-carboxylic acid, cis 4-(((2-((carboxymethoxy) methyl) cyclohexyl) methyl) thio) 1-((6-chloro 1,3-benzodioxol-5-yl) methyl) 2-propyl 1H-imidazole 5-carboxylic acid, trans 4-((4-(carboxymethyl) cyclohexyl) thio) 1-((6-chloro 1,3-benzodioxol-5-yl) methyl) 2-(1,3-dioxolan-2-yl) 1H-imidazole 5-carboxylic acid, 4-((4-(carboxymethyl) cyclohexyl) thio) 1-((6-chloro 1,3-benzodioxol-5-yl) methyl) 2-(2-furanyl) 1H-imidazole 5-carboxylic acid, trans 4-((4-(carboxymethyl) cyclohexyl) thio) 1-((6-chloro 1,3-benzodioxol-5-yl) methyl) 2-cyclopentyl 1H-imidazole 5-carboxylic acid, trans 3-((4-(carboxymethyl) cyclohexyl) thio) 1-((6-chloro 1,3-benzodioxol-5-yl) methyl) 2-(2-thienyl) 1H-imidazole 5-carboxylic acid, 4-((4-carboxycyclohexyl) thio) 1-((6-chloro 1,3-benzodioxol-5-yl) methyl) 2-(2-furanyl) 1H-imidazole 5-carboxylic acid, disodium salt of 4-((4-(carboxymethyl) cyclohexyl) thio) 1-((6-chloro 1,3-benzodioxol-5-yl) methyl) 2-propyl 1H-imidazole 5-carboxylic acid, dipotassium salt of 4-((4-(carboxymethyl) cyclohexyl) thio) 1-((6-chloro 1,3-benzodioxol-5-yl) methyl)

2-propyl 1H-imidazole 5-carboxylic acid, as well as the addition salts with pharmaceutically acceptable mineral or organic acids or mineral and organic bases The medicaments, which are a subject of the invention, can for example be used in the treatment of all vascular spasms, in the treatment of vasospasm following a cerebral haemorrhage, in the treatment of coronary spasms, peripheral vascular spasms as well as in the treatment of renal insufficiencies. These medicaments can also be used in the treatment of myocardial infarction, congestive cardiac insufficiency, in the prevention of the recurrence of post-angioplastic stenosis, cardiac and vascular fibroses, in the treatment of atherosclerosis, certain forms of hypertension such as in particular pulmonary hypertension, as well as in the treatment of asthma.

The medicaments, which are a subject of the invention, can also be used in the treatment of osteoporosis, prostatic hyperplasia and as neuronal protectors.

The invention extends to the pharmaceutical compositions containing at least one of the medicaments as defined above as active ingredient.

These pharmaceutical compositions can be administered by buccal, rectal route, by parenteral route or by local route as a topical application on the skin and mucous membranes or by injection by intravenous or intramuscular route.

These compositions can be solid or liquid and be presented in all the pharmaceutical forms commonly used in human medicine, such as, for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the patient being treated and the illness in question, can be, for example, 1 to 300 mg per day for an adult, by oral route or 1 to 100 mg per day by intravenous route.

Certain starting products of formulae (II) and (XVI) are known and can be prepared for example as indicated in the European Patent EP 168,950.

Other starting products of formulae (II) and (XVI) can in particular be prepared as indicated in the European Patent EP 0465368, or also in the examples described hereafter in the experimental part.

Certain starting products of formulae (II) and (XVI) are commercial products such as for example, the following products of formula (II):

2-propylimidazole, 2-isopropylimidazole, 2-ethylimidazole, 2-methylimidazole.

Examples of commercial products of formula (XVI) are given in patents EP 0465368 or EP 0503162.

In particular certain products of formulae (II) and (XVI) can also be prepared from the products of formula (II) for example by subjecting them to one or more of the reactions described above in a) to r), carried out under the conditions also described above.

Certain products of formula (XVI) can also be obtained by the monohalogenation of the product of formula (II) as defined above into the product of formula ($P_1$):

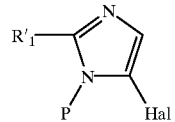

in which $R'_1$ and P have the meanings indicated above for the product of formula (II), which product of formula ($P_1$) can be reacted, after exchange according to the halogen metal reaction known to a man skilled in the art, with the appropriate electrophile, according to the methods known to a man skilled in the art and in particular for example following the same type of reaction described above for passing for example from the compound of formula (IX) to the compound of formula (XI).

Certain products of formula (XVI) can also be prepared according to the following diagram:

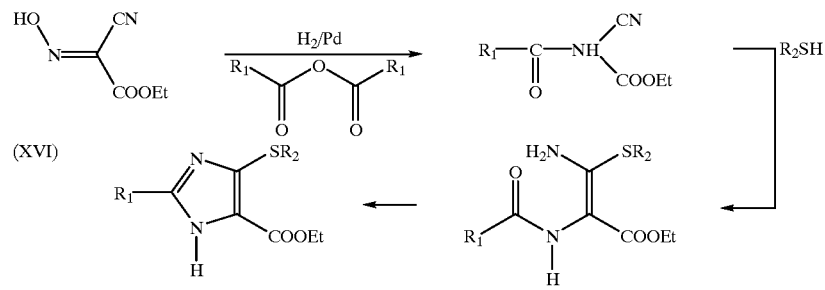

Certain products of formula (XVI) can also be prepared according to the following diagram:

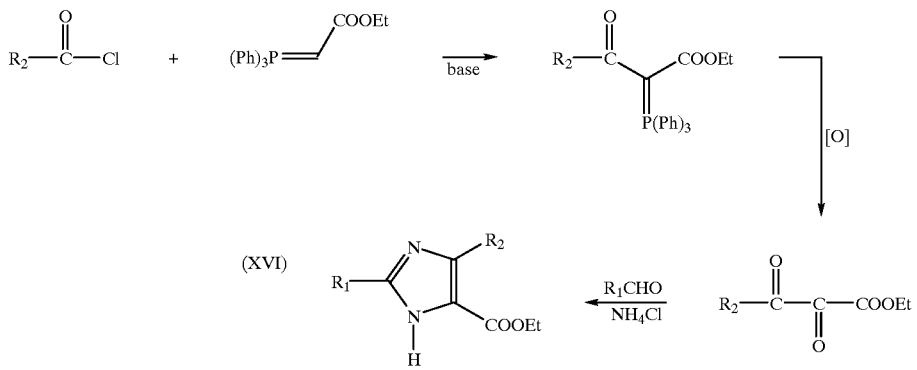

Certain products of formula (XVI) can also be prepared according to the following diagram:

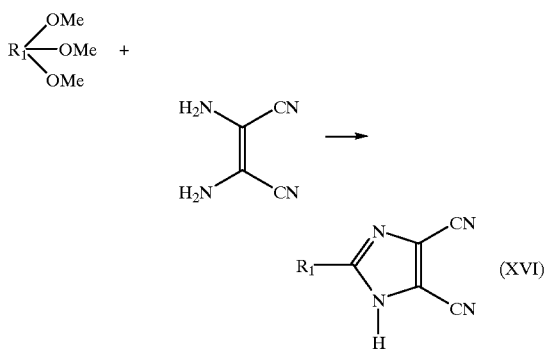

The starting compounds of formula (VI) such as 2,4,5-tribromoimidazole or also the starting products of formulae (XX) and (XXI) may be commercially available or can be prepared according to the usual methods known to a man skilled in the art.

The starting products of formula (X) are commercial products such as in particular:
methyl chloroformate
benzyl chloroformate
isobutyl chloroformate
ethyl chloroformate
N-propyl chloroformate The starting products of formulae (VIIIa) and (VIIIb) are commercial products such as in particular:
the following products of formula (VIIIa):
benzaldehyde or butanal
the following products of formula (VIIIb):
benzoyl or butyryl chloride.

A preparation process for some of the products of formula (III) is in particular described in the European Patent EP 0465368.

Examples of the preparation of the compounds of formula (III) are also described in the literature and examples of them are given in particular in the U.S. Pat. No. 4,880,804 or for example in the reference Chemistry and Industry 7 September 1987 HOWARD and COLQUHOUN pp. 612–617.

In particular, the product of formula (III) which is 6-chloro piperonyl chloride is commercially available from ACROS.

Finally a subject of the present invention is as new industrial products, the compounds of formulae (IV), (V), (IX), (XI) and (XIII) in which, it being understood that in the compounds of formulae (IX) and (XI), W represents the $CH_2—Y'$ radical, $Y'$ represents the phenyl radical substituted by a dioxol radical and optionally substituted by another substituent chosen from halogen atoms and alkoxy and alkyl radicals containing at most 4 carbon atoms and in which the ptional reactive functions are optionally protected by protective groups.

Thus a particular subject of the invention is the use of the products of formula (I) as defined above, for the preparation of pharmaceutical compositions intended for the treatment of illnesses resulting from an abnormal stimulation of the endothelin receptors and in particular intended for the treatment of hypertension induced by endothelin, of all vascular spasms, in the treatment of the after-effects of a cerebral haemorrhage, renal insufficiencies, myocardial infarction, cardiac insufficiency and in the prevention of the recurrence of post-angioplastic stenosis as well of cardiac and vascular fibroses.

The following examples illustrate the invention without however limiting it.

PREPARATION 1

Ethyl 4-bromo-cyclohexaneacetate

STAGE 1: ethyl 2-(4-bromocyclohexylidene)-ethyl acetate 8.07 g of triethylphosphonoacetate is introduced into 20 ml of tetrahydrofuran, the mixture is cooled down to 0° C. and 40 ml of a molar solution of lithium hexamethyldisilazane in tetrahydrofuran is added. After 15 minutes 6.5 g of 4-bromo-cyclohexanone (prepared as described in Heterocycles, Vol. 18, 1982 p. 163–167) is added and the whole is left for 1 hour at ambient temperature, followed by hydrolysis with a saturated solution of ammonium chloride, extraction with ethyl acetate, and after chromatography 8.5 g of the expected product (colourless oil) is obtained.

STAGE 2: ethyl 4-bromo-cyclohexaneacetate 3 g of the product obtained in Stage 1 above is introduced into 100 ml of ethanol, the whole is hydrogenated in the presence of platinum oxide as catalyst in order to produce after filtration 2.9 g of expected product (colourless oil).

EXAMPLE 1 ethyl 1-[(6-chloro-1,3-benzodioxol-5-yl) methyl]-4-[[4-(2-ethoxy-2-oxoethyl) cyclohexyl] thio]-2-propyl-1H-imidazole-5-carboxylate STAGE 1: ethyl cyano-[(1-oxobutyl) amino] acetate 5 g of ethyl (hydroxyimino) cyanoacetate, 40 cm³ of etrahydrofuran, 11.5 cm³ of butyric anhydride and 2.5 g of platinum are mixed together and the mixture is agitated under a hydrogen atmosphere until saturation is achieved. After filtering and rinsing with 5×15 cm³ of ethyl ether, the ether is evaporated off, 200 cm³ of essence G is added little by little, followed by separating, washing with 3×10 cm³ of essence G and drying at approximately 75° C. Concentration is carried out to ~10 cm³, 50 cm³ of essence G is added, the whole is left to crystallize for 30 mn at ambient temperature, followed by separation, washing with 3×3 cm³ of essence G and drying at approximately 75° C. 5.73 g of product is obtained. M.P.=110° C. Recrystallization for analyses:

540 mg of the product obtained is dissolved in 50 cm³ of isopropyl ether under reflux, the solution is filtered, concentrated, left for approximately 1 hour at rest at ambient temperature, followed by separating, washing with isopropyl ether and drying. 440 mg of expected product is obtained. M.P.=110° C.

Microanalysis for $C_9H_{14}N_2O_3$=198.22

|  | C | H | N | O |
|---|---|---|---|---|
| % calculated | 54.53 | 7.12 | 14.13 | 24.22 |
| % found | 54.5 | 7.2 | 14.0 |  |

| IR Spectrum CHCl₃ | | |
|---|---|---|
| =C—NH | ~3430 cm⁻¹ | |
| —C≡N | ~2245 cm⁻¹ | |
| C=O | 1758 cm⁻¹ | ester |
|  | 1692 cm⁻¹ | amide |
| Amide II | 1492 cm⁻¹ | |

Stage 2: ethyl 3-amino 2-[(1-oxobutyl) amino] 3-(methylthio) 2-propenoate 1.4 ml of triethylamine is added to a solution of 20 g of the nitrile obtained in Stage A above in 400 ml of ethanol, the reaction medium is cooled down to approximately −10° C. and approximately 22 g of methylmercaptan is introduced by bubbling it through. Agitation is carried out for approximately 72 hours at 0° C. The excess methanethiol is eliminated, the ethanol is driven off, followed by impasting in essence G, filtering and drying. 24.3 g of expected product (colourless crystals) is obtained. M.P.$_{K115}$=120–124° C.

Microanalysis for $C_{10}H_{18}N_2O_3S$=246.33

|  | C | H | N | S | O |
|---|---|---|---|---|---|
| % calculated | 48.76 | 7.37 | 11.37 | 13.02 | 19.49 |
| % found | 48.6 | 7.5 | 11.4 | 12.6 | — |

| IR Spectrum CHCl₃ | |
|---|---|
| =C—NH₂ | 3500, 3412 cm⁻¹ |
| =C—NH | 3365, 3275 cm⁻¹ |
| C=O complex | 1665 cm⁻¹ |
| C=C and NH₂ def. | 1592 cm⁻¹ |
| Amide II | 1488 cm⁻¹ |

| UV Spectrum in EtOH | |
|---|---|
| Max. 220 nm | ε = 5500 |
| Max. 291–292 | ε = 19400 |

Stage 3: ethyl 4-(methylthio) 2-propyl 1H-imidazole 5-carboxylate

A solution of 12.9 g of 4-dimethylaminopyridine in 90 cm³ of methylene chloride is added to 20.1 g of phosphorus pentachloride in 300 cm³ of methylene chloride, cooled down to approximately −70° C.

The reaction medium is further maintained for approximately 15 mn at approximately −70° C. then a solution of 12 g of the product obtained in Stage B above in 120 cm³ of methylene chloride is introduced. The whole is left to return at ambient temperature and is maintained under agitation for approximately 22 hours.

The reaction mixture is poured into 2.5 litres of water+ice and neutralized by the addition of approximately 60 g of sodium bicarbonate. Agitation is carried out again for approximately 30 minutes, followed by decanting and extraction with 500 cm³ of methylene chloride. After washing with salt water and drying, the solvent is driven off at approximately 50° C. Purification is carried out by chromatography on silica eluting with methylene chloride-ethyl acetate (90-10) then methylene chloride-ethyl acetate (80-20). The solvents are driven off at approximately 50° C., followed by impasting with essence G, filtering and drying. 7.4 g of expected product (colourless crystals) is obtained. M.P.$_{K95}$=85° C. Microanalysis Concordance for $C_{10}H_{16}N_2O_2S$=228.32

|  | C | H | N | S | O |
|---|---|---|---|---|---|
| % calculated | 52.61 | 7.06 | 12.27 | 14.04 | 14.02 |
| % found | 52.7 | 7.3 | 12.2 | 14.0 | |

| IR Spectrum CHCl₃ | |
|---|---|
| =C—NH | 3440–3260 cm⁻¹ |
| C=O complex max. | ~1672 cm⁻¹ |
| Heterocycle | 1542–1498 cm⁻¹ |

| UV Spectrum in EtOH | |
|---|---|
| Max. 213–214 nm | ε = 14500 |
| Infl. 229 nm | ε = 7200 |
| Max. 286 nm | ε = 12200 |

| UV Spectrum in EtOH/HCl N/10 | |
|---|---|
| Max. 238 nm | ε = 6800 |
| Max. 277 nm | ε = 9600 |
| return to base → max. 296 nm. | |

STAGE 4: ethyl 1-[(6-chloro-1,3-benzodioxol-5-yl) methyl]-4-(methylthio)-2-propyl-1H-imidazole-5-carboxylate 10 g of the product obtained in Stage 3 above and 13.5 g of 6-chloro piperonyl chloride are introduced into 100 ml of dimethyl formamide, 9 g of potassium carbonate is added and the whole is heated to 100° C. for one hour. The reaction medium is cooled down to ambient temperature, then poured onto ice, the precipitate obtained is filtered out then impasted in isopropyl ether. In this way 9.25 g of expected product is obtained.

STAGE 5: ethyl 1-[(6-chloro-1,3-benzodioxol-5-yl) methyl]-4-(methylsulphinyl)-2-propyl-1H-imidazole-5-carboxylate 9.26 g of the product obtained in Stage 4 above is introduced into 400 ml of methylene chloride at 0° C. and 5.8 g of metachloroperbenzoic acid is added. Agitation is carried out for one hour at ambient temperature and the reaction medium is washed with sodium and potassium hydride, followed by extraction with methylene chloride, washing with water, drying and evaporating the solvent. After chromatography 8.8 g of expected product is obtained. M.p.=187° C.

STAGE 6: ethyl 1-[(6-chloro-1,3-benzodioxol-5-yl) methyl]-4-mercapto-2-propyl-1H-imidazole-5-carboxylate 800 mg of the product obtained in Stage 5 above is introduced into 16 ml of methylene chloride and 0.54 ml of trifluoroacetic anhydride is added. Agitation is carried out for 30 minutes, followed by evaporating to dryness and the residue is taken up in 10 ml of methanol and 4 ml of triethylamine. Agitation is carried out for 30 minutes, followed by extraction with chloroform, washing with a saturated solution of ammonium chloride, drying and evaporating to dryness. In this way 720 mg of expected product is obtained.

STAGE 7: ethyl 1-[(6-chloro-1,3-benzodioxol-5-yl) methyl]-4-[[4-(2-ethoxy-2-oxoethyl) cyclohexyl] thio]-2-propyl-1H-imidazole-5-carboxylate 1 g of the product obtained in Stage 6 above is introduced into dimethylformamide, 146 mg of a suspension of sodium hydride at 60% in oil is added and the reaction medium is left under agitation for 15 minutes at ambient temperature. Then 1.08 mg of the product obtained in Stage 2 of Preparation 1 is added, and the reaction medium is left under agitation for 24 hours at ambient temperature, followed by hydrolysis with a saturated solution of ammonium chloride and extraction with ethyl acetate. In this way, after chromatography, 1.1 g of expected product (amorphous solid) is obtained.

EXAMPLE 2

4-((4-(carboxymethyl) cyclohexyl) thio)-1-((6-chloro-1,3-benzodioxol-5-yl) methyl)-2-propyl-1H-imidazole-5-carboxylic acid 760 mg of the product of Example 1 is introduced into 20 ml of tetrahydrofuran, 50 ml of ethanol and 25 ml of 2N soda are added and the whole is left for 24 hours at ambient temperature. The tetrahydrofuran and the ethanol are evaporated off then the reaction medium is acidified to pH 1. After extraction with ethyl acetate and evaporating to dryness, the residue is recrystallized from ethanol. 490 mg of expected product is obtained. M.p.=166° C.

EXAMPLE 3

4-((5-(carboxypentyl) thio)-1-((6-chloro 1,3-benzodioxol-5-yl) methyl)-2-(1,3-dioxolan-2-yl)-1H-imidazole-5-carboxylic acid STAGE 1: 1-((6-chloro-1,3-benzodioxol-5-yl)-methyl)-2,4,5-tribromo-1H-imidazole 25 g of 2,4,5-tribromoimidazole is introduced into 500 ml of dimethylformamide and 4.3 g of sodium hydride is added. Agitation is maintained for 10 minutes at ambient temperature. Next 18.4 g of 6-chloro piperonyl chloride, then 25 g of sodium iodide are added to the reaction medium and agitation is continued for 15 minutes at ambient temperature.

The reaction medium is finally poured into 3 litres of water, separated, washed abundantly with water, then successively with 250 ml of ethanol, 250 ml of isopropanol, then finally with 250 ml of isopropyl ether.

After drying, 31.5 g of expected product (cream solid) is collected M.p.=225° C. IR CHCl$_3$ (cm$^{-1}$) Absence of =C—NH

| Aromatic heterocycle | 1624–1506–1497–1485 |

STAGE 2: 4,5-dibromo-1-[(6-chloro-1,3-benzodioxol-5-yl)-methyl]-1h-imidazole-2-carboxaldehyde 20 g of the product obtained in Stage 1 above is introduced into 200 ml of anhydrous methylene chloride to which 500 ml of anhydrous ethyl ether is added. A 3M solution of ethyl magnesium bromide in ethyl ether is added and the whole is left under agitation for 20 minutes at ambient temperature. Then an excess (15 ml) of anhydrous dimethylformamide is added. After 2 hours at ambient temperature, hydrolysis is carried out with 200 ml of 1N hydrochloric acid followed by extraction 3 times with 300 ml of ethyl acetate. The organic phase is washed with saturated sodium chloride then dried and evaporated to dryness. In this way 14.5 g of expected product is obtained.

STAGE 3: 4,5-dibromo-1-[(6-chloro-1,3-benzodioxol-5-yl) methyl]-2-(1,3-dioxolan-2yl)-1H-imidazole The product obtained in Stage 2 above is introduced into 200 ml of toluene, 20 ml of ethylene glycol is added and the reaction medium is taken to reflux overnight then evaporated to dryness. 200 ml of a saturated solution of sodium hydrogen carbonate is added which is extracted 3 times with 200 ml of ethyl acetate. The organic phase is washed with saturated sodium chloride, then dried and evaporated to dryness. The residue obtained is impasted in isopropyl ether, filtered and dried. In this way 13.5 g of expected product (solid) is obtained. M.p.=188° C.

STAGE 4: 4-bromo-1-[(6-chloro-1,3-benzodioxol-5-yl) methyl]-2-(1,3-dioxolan-2-yl)-1H-imidazole-5-carboxaldehyde 10 g of the product obtained in Stage 3 above is introduced into 200 ml of anhydrous tetrahydrofuran. 10 ml of ethyl magnesium bromide (3M solution in ethyl ether) is added and the reaction medium is left under agitation for 20 minutes at ambient temperature. Then an excess of anhydrous dimethylformamide is added. After 2 hours at ambient temperature, hydrolysis is carried out with 200 ml of 1N hydrochloric acid and extraction is carried out 3 times with 300 ml of ethyl acetate. The organic phase is washed with saturated sodium chloride then dried and evaporated to dryness. The residue obtained is impasted in isopropyl ether. In this way 7.6 g of expected product is obtained, which is used without purification for the following stage.

STAGE 5: ethyl 6-[[1-[(6-chloro-1,3-benzodioxol-5-yl) methyl]-2-(1,3-dioxolan-2-yl)-5-formyl-1H-imidazol-4-yl] thio]-hexanoate 3.9 g of ethyl 6-mercaptohexanoate is dissolved in 200 ml of anhydrous dimethylformamide, 1.1 g of sodium hydride at 50% in oil is added and the reaction medium is left for 20 minutes at ambient temperature. Then 7.6 g of the product obtained in Stage 4 above is added, and the whole is left overnight at ambient temperature. The dimethyl-formamide is evaporated off under vacuum, the residue is taken up in 200 ml of saturated ammonium chloride and extraction is carried out with three times 200 ml of methylene chloride. The organic phases are dried, filtered and evaporated to dryness. The residue is impasted in isopropyl ether and filtered. In this way 5.8 g of expected product (solid) is obtained.

STAGE 6: 4-((5-(carboxypentyl) thio) 1-((6-chloro 1,3-benzodioxol-5-yl) methyl) 2-(1,3-dioxolan-2-yl)-1H-imidazole-5-carboxylic acid 5.1 g of the product obtained in Stage 5 above is introduced into 100 ml of methylene chloride, 500 ml of methanol is added then by fractions: 22 g of manganese oxide, 2.2 g of sodium cyanide and 1.5 ml of acetic acid are added. The reaction medium is left under agitation for 72 hours at ambient temperature, then filtered and washed with methylene chloride. The organic phase is washed with saturated sodium chloride then dried and evaporated to dryness. The residue obtained is chromatographed on silica to give 3.1 g of intermediate methyl ester which is saponified in a mixture of 2N soda/ethanol to give 2.5 g of expected product. M.p.=175° C.

EXAMPLE 4

4-((5-(carboxypentyl) thio) 1-((6-chloro 1,3-benzodioxol-5-yl) methyl) 2-(methoxymethyl)-1H-imidazole-5-carboxylic acid STAGE 1: 4,5-dibromo-1-[(6-chloro-1,3-benzodioxol-5-yl) methyl]-2-(methoxymethyl)-1H-imidazole 28.2 g of the product obtained in Stage 1 of Example 3 is introduced into 400 ml of ethanol, 2.5 g of sodium borohydride is added and after 2 hours, 10 ml of acetic acid is added. Agitation is carried out for 15 minutes, followed by evaporating to dryness, the residue is impasted in isopropyl ether, filtered and 27.5 g of a cream solid is obtained. The 27.5 g obtained previously is dissolved in 400 ml of tetrahydrofuran, 3.73 g of sodium hydride at 50% in oil is added, agitation is carried out for 15 minutes and 4.5 ml of methyl iodide is added. The reaction medium is left overnight at ambient temperature, extracted with ethyl acetate and after chromatography, 18.7 g of expected product is obtained.

STAGE 2: 4-((5-(carboxypentyl) thio)-1-((6-chloro 1,3-benzodioxol-5-yl) methyl) 2-(methoxymethyl)-1H-imidazole-5-carboxylic acid The operation is carried out as in Stages 4, 5 and 6 of Example 3 starting with the product obtained in Stage 1 above and in this way the expected product is obtained. M.p.=170° C.

EXAMPLE 5 ethyl 1-[(6-chloro-1,3-benzodioxol-5-yl) methyl]-4-[(6-ethoxy-6-oxohexyl) thio]-2-propyl-1H-imidazole-5-carboxylate The operation is carried out as in Stage 7 of Example 1 starting with the product obtained in Stage 6 of Example 1 and ethyl 6-bromo-hexanoate instead of ethyl 4-bromocyclohexaneacetate.

In this way the expected product is obtained.

EXAMPLE 6

4-((5-(carboxypentyl) thio) 1-((6-chloro 1,3-benzodioxol-5-yl) methyl)-2-propyl-1H-imidazole-5-carboxylic acid The operation is carried out as in Example 2 starting with the product of Example 5 and in this way the expected product is obtained. M.p.=145° C.

EXAMPLE 7 ethyl 1-[(6-chloro-1,3-benzodioxol-5-yl) methyl]-4-[(5-ethoxy-5-oxopentyl) thio]-2-propyl-1H-imidazole-5-carboxylate The operation is carried out as in Stage 7 of Example 1 starting with the product obtained in Stage 6 of Example 1 and ethyl 5-bromo-pentanoate instead of ethyl 4-bromocyclohexaneacetate. In this way the expected product is obtained.

EXAMPLE 8

4-((4-carboxybutyl) thio)-1-((6-chloro-1,3-benzodioxol-5-yl) methyl)-2-(propyl)-1H-imidazole-5-carboxylic acid The operation is carried out as in Example 2 starting with the product of Example 7 and in this way the expected product is obtained. M.p.=156° C.

EXAMPLE 9 ethyl 1-[(6-chloro-1,3-benzodioxol-5-yl) methyl]-4-[[4-(2-ethoxy-2-oxoethylidene) cyclohexyl] thio]-2-propyl-1H-imidazole-5-carboxylate 1.1 g of the product obtained in Stage 6 of Example 1 is introduced, 127 mg of a suspension of sodium hydride at 50% in oil is added and the reaction medium is left under agitation for 15 minutes at ambient temperature. Then 657 mg of the product obtained in Stage 1 of Preparation 1 is added and the reaction medium is left under agitation for 24 hours at ambient temperature, followed by hydrolysis with a saturated solution of ammonium chloride and extraction with ethyl acetate and after chromatography, 880 mg of the expected product (amorphous solid) is obtained.

EXAMPLE 10

4-((4-(carboxymethylene) cyclohexyl) thio)-1-((6-chloro 1,3-benzodioxol-5-yl) methyl)-2-propyl-1H-imidazole-5-carboxylic acid 880 mg of the product of Example 9 is introduced into 20 ml of tetrahydrofuran, 50 ml of ethanol and 25 ml of 2N soda are added and the reaction medium is left for 24 hours at ambient temperature. The tetrahydrofuran and the ethanol are evaporated off, then the reaction medium is acidified to pH 1. Extraction is carried out with ethyl acetate, followed by evaporation to dryness and the residue is recrystallized from ethyl acetate. In this way 490 mg of expected product is obtained. M.p.=168° C.

EXAMPLE 11 ethyl 2-butyl-1-[(6-chloro-1,3-benzodioxol-5-yl)-methyl]-4[ (6-ethoxy-6-oxohexyl) thio]-1H-imidazole-5-carboxylate The operation is carried out as in Example 1, using in Stage 4 of Example 1 ethyl 2-n-butyl-4-(methylthio)-1H-imidazole-5-carboxylate obtained as indicated in Stage d) of Example 56 of EP 0503162 instead of ethyl 2-n-propyl-4-(methylthio)-1H-imidazole-5-carboxylate and using in Stage 7 of Example 1 ethyl 6-bromohexanoate instead of ethyl 4-bromocyclohexaneacetate. In this way the expected product is obtained in the form of a yellow oil.

EXAMPLE 12

2-butyl 4-((5-carboxypentyl) thio) 1-((6-chloro 1,3-benzodioxol-5-yl) methyl)-1H-imidazole-5-carboxylic acid The operation is carried out as in Example 2 starting with the product of Example 11. In this way the expected product is obtained. M.p. 128° C.

By operating as in Stage 7 of Example 1 and Example 2, starting with ethyl 1-((6-chloro 1,3-benzodioxol-5-yl) methyl) 4-mercapto 2-propyl 1H-imidazole 5-carboxylate obtained as indicated in Example 1 Stage 6 and the appropriate halogenated or tosylated derivative, the products of the following examples were prepared:

EXAMPLE 13

1-((6-chloro 1,3-benzodioxol-5-yl) methyl) 4-((4-carboxycyclohexyl) thio) 2-propyl 1H-imidazole 5-carboxylic acid (cis/trans). M.p.=174° C.

EXAMPLE 14

4-(((4-carboxycyclohexyl) methyl) thio) 1-((6-chloro 1,3-benzodioxol-5-yl) methyl) 2-propyl 1H-imidazole 5-carboxylic acid (cis/trans). M.p.=184° C.

EXAMPLE 15

4-(((3-carboxycyclohexyl) methyl) thio) 1-((6-chloro 1,3-benzodioxol-5-yl) methyl) 2-propyl 1H-imidazole 5-carboxylic acid (diastereoisomers). M.p.=178° C.

EXAMPLE 16 cis 4-(((2-((carboxymethoxy) methyl) cyclohexyl) methyl) thio) 1-((6-chloro 1,3-benzodioxol-5-yl) methyl) 2-propyl 1H-imidazole 5-carboxylic acid (diastereoisomers). M.p.=172° C.

Preparation of the Reagents Used at the Start of Examples 13 to 16.

1) Preparation of ethyl 4-bromo cyclohexyl carboxylate used at the start of Example 13.

0.9 ml of phosphorus tribromide is introduced slowly into 5 ml of ethyl (4-hydroxycyclohexyl) carboxylate and the reaction medium is heated at 80° C. for 6 hours. The whole is left to return to ambient temperature, followed by washing with salt water, extraction with ethyl acetate, drying and evaporating the solvent under reduced pressure. The residue is chromatographed on silica (eluant: AcOEt-cyclohexane 10–90) and 3.51 g of expected product is obtained.

2) Preparation of ethyl 1-((4-tosyloxymethyl) cyclohexyl) arboxylate used at the start of Example 14.

1 g of 1,4-dihydroxymethyl cyclohexane in 10 ml of dimethylformamide is agitated for 5 hours at ambient temperature in the presence of 0.94 g of imidazole and 1.8 ml of diphenyl trimethyl silane chloride then the whole is poured into a saturated aqueous solution of ammonium chloride, followed by extraction with ethyl acetate, washing with salt water and drying, the solvent is evaporated off under reduced pressure, the residue is chromatographed on silica (eluant: $CH_2Cl_2$-AcOEt 95-5). 1.31 g of silylated derivative is obtained. 13.06 g of silylated derivative prepared as indicated above in 260 ml of dimethylformamide is agitated for 40 hours at ambient temperature with 45 g of pyridinium dichromate, then partially concentrated under reduced pressure, the reaction medium is poured into 400 ml of ice-cooled hydrochloric acid (N), extracted with ethyl acetate, followed by washing with a solution of sodium bicarbonate, drying, the solvent is evaporated off under reduced pressure and 13.1 g of crude acid is obtained. 12.53 g of the acid obtained above in 125 ml of 1000 ethanol is agitated for 70 hours at ambient temperature in the presence of 10 ml of chlorotrimethylsilane then the solvents are evaporated off under reduced pressure. After chromatography on silica (eluant $CH_2Cl_2$-AcOEt 95-5 to 80-20), 3.40 g of unblocked ester is obtained. Formation of the tosylate.

3.40 g of the preceding derivative in 10 ml of pyridine is cooled down to 0°/+5° C., 5.22 g of tosyl chloride in 25 ml of dichloromethane is added over 50 minutes and agitation is carried out for 20 hours at ambient temperature. The reaction medium is poured into 200 ml of N hydrochloric acid, followed by extraction with dichloromethane, washing with water and drying, the solvent is evaporated off under reduced pressure, the residue is chromatographed on silica (eluant: cyclohexane/AcOEt 2-8) and 5.50 g of expected tosylate is obtained 3) Preparation of ethyl 1-((3-tosyloxymethyl) cyclohexyl) carboxylate used at the start of Example 15.
Formation of the Acid Chloride 5 g of 1,3-cyclohexane dicarboxylic acid in 10 ml of thionyl chloride is agitated for 3 hours under reflux, the excess reagent is distilled off, the residue is taken up in toluene, the solvent is evaporated off and 6.04 g of expected product is collected.
Formation of the Ester 1.69 ml of ethanol and 50 ml of tetrahydrofuran are cooled down to 0° C., 18.12 ml of n-butyllithium in solution in tetrahydrofuran (1.6 M/l) is added over 30 minutes and agitation is carried out for 30 minutes at 0°/+5° C. This solution is added over 30 minutes to 6.04 g of the acid chloride obtained previously in 60 ml of tetrahydrofuran at a temperature below 10° C.
Reduction into the Alcohol While maintaining this temperature, 58 ml of lithium tri(terbutoxyalumino hydride) is added over 30 minutes, agitation is carried out for 1 hour, the reaction medium is poured into N hydrochloric acid, followed by extraction with ethyl acetate, washing with salt water, drying and evaporating under reduced pressure, the residue is chromatographed (eluant: $CH_2Cl_2$/AcOEt 9-1) and 1.37 g of the alcohol is obtained.
Formation of the Tosylate 1.33 g of the preceding alcohol in 5 ml of pyridine is cooled down to 0°/+5° C., 1.63 g of tosyl chloride in 5 ml of dichloromethane is added over 20 minutes and agitation is carried out for 20 hours at ambient temperature. The reaction medium is poured into 100 ml of N hydrochloric acid, followed by extraction with ethyl acetate, washing with water and drying, the solvent is evaporated off under reduced pressure, the residue is chromatographed on silica (eluant: $CH_2Cl_2$) and 1.97 g of expected tosylate is obtained.

4) Preparation of ethyl 1-((2-tosyloxymethyl) cyclohexyl) carboxylate used at the start of Example 16.
Formation of the Ester 2.23 ml of ethyl diazoacetate in solution in 16 ml of dichloromethane is added over 1 hour at ambient temperature to 3.06 g of cis 1,2-cyclohexane dimethanol in 100 ml of dichloromethane in the presence of a few drops of ethyl etherate borotrifluoride. The reaction medium is maintained under agitation for 16 hours at ambient temperature, followed by washing with water and drying, the solvent is evaporated off under reduced pressure, the residue is chromatographed on silica (eluant: AcOEt/cyclohexane 20-80) and 1.98 g of expected product is obtained.
Formation of the Tosylate 1.01 g of the preceding product in 5 ml of pyridine is cooled down to 0°/+5° C., 1.00 g of tosyl chloride in 5 ml of dichloromethane is added over 30 minutes and agitation is carried out for 16 hours at ambient temperature. The reaction medium is poured into 100 ml of N hydrochloric acid, followed by extraction with dichloromethane, washing with water and drying, the solvent is evaporated off under reduced pressure, the residue is chromatographed on silica (eluant: cyclohexane/AcOEt 2-8) and 1.38 g of expected tosylate is obtained.

EXAMPLE 17 trans 4-((4-(carboxymethyl) cyclohexyl) thio) 1-((6-chloro 1,3-benzodioxol-5-yl) methyl) 2-(1,3-dioxolan-2-yl) 1H-imidazole 5-carboxylic acid.

Stage A: ethyl amino (cyano) acetate.

20 g of ethyl cyano (hydroxyimino) acetate is suspended in 200 ml of water. A saturated solution of sodium bicarbonate prepared with 16 g of $NaHCO_3$ and 160 ml of water is added over 15 minutes at ambient temperature. The reaction medium is heated to 35° C., 68 g of sodium dithionite is added, over 15 minutes, the whole is left to return to ambient temperature. The medium is saturated with NaCl. After extraction with 5 times 500 ml of $CH_2Cl_2$ the organic phases are dried and concentrated under reduced pressure and 12.75 g of expected product is obtained.

Stage B: ethyl ((acetyloxyacetyl) amino) cyano acetate.

24.3 g of acetoxyacetyl chloride in solution in 60 ml of tetrahydrofuran is added to 23 g of the product obtained as in Stage A in 10 ml of tetrahydrofuran in the presence of 10 ml of pyridine. Agitation is carried out at ambient temperature for 4 hours, the solvent is evaporated off, the residue is taken up in ethyl acetate, followed by washing with salt water and drying, the solvent is evaporated off under reduced pressure, the residue is crystallized form ethyl ether and 27.59 g of expected product is obtained. M.p.=82° C.

Stage C: ethyl 3-((2-((acetyloxyacetyl) amino) 3-(amino (4-methoxyphenyl) methyl) thio) 2-propenoate.

33.4 ml of 4-methoxy benzyl mercaptan is added dropwise to 27.59 g of the product obtained in Stage B in solution in 500 ml of ethanol and in the presence 5 ml of triethylamine. Agitation is carried out for 16 hours at ambient temperature, the solvent is evaporated off under reduced pressure, followed by crystallization from ethyl ether, separation and drying under reduced pressure. 33.7 g of expected product is obtained. M.p.=145° C.

Stage D: ethyl 2-((acetyloxy) methyl) 5-(((4-methoxyphenyl) methyl) thio) 1H-imidazole 4-carboxylate.

2.3 g of the product obtained in Stage C in 50 ml of ethyl acetate is heated under reflux, 3.16 ml of propane 1-phosphonic anhydride at 50% in ethyl acetate is added, agitation is carried out for 30 minutes, the whole is left to cool down and neutralized with a saturated aqueous solution of sodium bicarbonate. Extraction is carried out with ethyl acetate, followed by washing with salt water and drying, the solvent is evaporated off and after impasting in ether and drying, 2.09 g of expected product is obtained. M.p.=126° C.

Stage E: ethyl 2-(hydroxymethyl) 5-(((4-methoxyphenyl) methyl) thio) 1H-imidazole 4-carboxylate.

26 g of the product obtained as in Stage D in 600 ml of ethanol is heated under reflux for 5 days in the presence of 1.3 g of paratoluene sulphonic acid. The solvent is evaporated off under reduced pressure, the residue is taken up in ethanol and 6 g of expected product is obtained. After concentration of the mothers liquors and chromatography on silica (eluant: AcOEt-cyclohexane 5–5), 9.44 g of additional expected product is collected.

Stage F: ethyl 2-formyl 5-(((4-methoxyphenyl) methyl) thio) 1H-imidazole 4-carboxylate. 8.6 g of the product obtained in Stage 6 in 300 ml of dichloromethane and 100 ml of methanol is agitated for 1 hour at ambient temperature in the presence of 43 g of manganese. After filtering, the solvent of the solution obtained is evaporated off under reduced pressure and 6 g of expected product is obtained which is used as it is for the following stage.

Stage G: ethyl 1-((6-chloro 1,3-benzodioxol-5-yl) methyl) 2-formyl 4-(((4-methoxyphenyl) methyl) thio) 1H-imidazole 5- carboxylate.

3 g of the product obtained in Stage F in 150 ml of dimethylformamide is agitated at ambient temperature for 50 hours with 2.58 g of potassium carbonate and 2.87 g of 6-chloropiperonyl chloride. Another 1.5 g of chlorinated reagent is added and agitation is carried out for 48 hours. The solvent is evaporated off under reduced pressure, the residue is taken up in 150 ml of a saturated aqueous solution of ammonium chloride, followed by extraction with ethyl acetate, washing with salt water and drying, the solvent is evaporated off, the residue is chromatographed on silica (eluant: AcOEt-cyclohexane 2–8) and after impasting in isopropyl ether 3.71 g of expected product is obtained.

Stage H: mercury bis ((1-((6-chloro 1,3-benzodioxol-5-yl) methyl) 2-formyl 5-ethoxycarbonyl 1H-imidazol-4-yl) thiolate).

A suspension containing 2.6 g of the product obtained as in Stage G in 2.6 ml of anisole and 13 ml of trifluoroacetic acid is cooled down to 0° C. 1.13 g of mercury trifluoroacetate is added, the reaction medium is left to return to ambient temperature, agitation is carried out for 2 hours, the solvent is evaporated off under reduced pressure, the residue is taken up in ethanol, the mercury salt obtained is separated and dried. 1.83 g of expected product is collected.

Stage I: mercury bis ((1-((6-chloro 1,3-benzodioxol-5-yl) methyl) 2-(1,3-dioxolan-2-yl) 5-ethoxycarbonyl 1H-imidazol-4-yl) thiolate).

500 mg of the product obtained in Stage H in 100 ml of toluene is heated under reflux with 165 mg of ethylene glycol and 25 mg of paratoluene sulphonic acid, while eliminating the water formed. The solvent is evaporated off under reduced pressure, the crystals formed are separated and dried. After concentration of the mothers liquors and impasting in ethyl ether, the additional crystallized product is separated and dried. 540 mg of expected product is obtained. M.p.=186 C.

Stage J: ethyl 1-((6-chloro 1,3-benzodioxol-5-yl) methyl) 2-(1,3-dioxolan-2-yl) 4-mercapto 1H-imidazole 5-carboxylate.

A current of hydrogen sulphide is bubbled for 10 minutes through a mixture containing 530 mg of the product obtained in Stage I in 100 ml of ethyl acetate, followed by filtering, washing with ethyl acetate, concentrating under reduced pressure and 500 mg of expected product is obtained which is used as it is for the following stage.

Stage K: ethyl trans 1-((6-chloro 1,3-benzodioxol-5-yl) methyl) 2-(1,3-dioxolan-2-yl) 4-(4-(((ethoxycarbonyl) methyl) cyclohexyl) thio) 1H-imidazole 5-carboxylate.

60 mg of sodium hydride at 50% in oil is added to 500 mg of the product obtained in Stage J in solution in 20 ml of N, N-dimethylformamide, agitation is carried out for 15 minutes, 610 mg of ethyl 4-iodo cyclohexane acetate is added and the reaction medium is maintained under agitation for 16 hours. 50 ml of a saturated aqueous solution of ammonium chloride is added, extraction is carried out with dichloromethane, the organic phase is washed with salt water, the solvent is evaporated off under reduced pressure and the residue is chromatographed on silica (eluant: AcOEt-cyclohexane 3-7). 380 mg of expected product is obtained.

Stage L: trans 4-((4-(carboxymethyl) cyclohexyl) thio) 1-((6-chloro 1,3-benzodioxol-5-yl) methyl) 2-(1,3-dioxolan-2-yl) 1H-imidazole 5-carboxylic acid.

380 mg of the product obtained in Stage K, 20 ml of 2N soda and 20 ml of ethanol are mixed together, tetrahydrofuran is added until dissolution is obtained and the reaction medium is maintained under agitation at ambient temperature for 2 days. The solvent is evaporated off under reduced pressure, the residue is taken up in water, acidified to pH=1 with 2N hydrochloric acid, followed by filtering, washing with water, drying under reduced pressure at 60° C. and 280 mg of expected product is collected. M.p.=171° C. Preparation of ethyl 4-iodo cyclohexane acetate used in Stage K of Example 17.

Stage a: trans 4-iodo cyclohexanol.

44 g of 7-oxabicyclo [2.2.1] heptane is poured dropwise into 250 ml of 57% hydroiodic acid while maintaining the reaction medium at ambient temperature and under agitation for 4 hours. The reaction medium is poured into ice-cooled water and extracted with ethyl ether, the ethereal phases are washed with 200 ml of 0.5N sodium thiosulphate, washed with salt water, dried and the solvents are evaporated off. 96.47 g of expected product is obtained. M.p.=53.4° C.

Stage b: 4-iodo cyclohexanone.

52.4 g of potassium permanganate is added to 50 g of the product obtained in Stage a) in solution in 500 ml of acetonitrile. Agitation is carried out for 16 hours at ambient temperature, followed by filtering, the solvent is evaporated off under reduced pressure, the residue is chromatographed on silica (eluant: AcOEt-cyclohexane 20-80) and 36.17 g of expected product is obtained. M.p.=48.7° C.

Stage c: ethyl 4-iodo cyclohexylidene acetate.

6.6 g of sodium hydride at 60% in oil then 36.04 g of the product obtained in Stage b) dissolved in 100 ml of tetrahydrofuran are added slowly to a mixture containing 32 ml of triethylphosphonoacetate in 200 ml of tetrahydrofuran. The reaction medium is maintained under agitation at ambient temperature, two lots of 2 g of sodium hydride are added then the reaction medium is poured into water and neutralized by the addition of 150 ml of a saturated aqueous solution of ammonium chloride. Extraction is carried out with ethyl acetate, followed by washing with salt water and drying, the solvents are evaporated off under reduced pressure, purification is carried out by chromatography on silica (eluant: AcOEt-cyclohexane 3-7) and 38.25 g of expected product is obtained.

Stage d: ethyl 4-iodo cyclohexane acetate.

A mixture containing 38.25 g of the product obtained in Stage c), 300 ml of tetrahydrofuran and 1.5 g of platinum oxide then 5 g of platinum at 5% on activated charcoal is hydrogenated under 600 mbars of pressure for 48 hours. After filtering, the solvent is evaporated off under reduced pressure, the residue is chromatographed on silica (eluant AcOEt-cyclohexane 10-90) and 27.01 g of expected product is obtained.

By operating as in Example 17 omitting Stages E, F and I, using at the start the product obtained in Example 17 Stage A and the appropriate acid chloride, the following products were prepared:

EXAMPLE 18 trans 4-((4-(carboxymethyl) cyclohexyl) thio) 1-((6-chloro 1,3-benzodioxol-5-yl) methyl) 2-(2-furanyl) 1H-imidazole 5-carboxylic acid. M.p.=185° C.

EXAMPLE 19 trans 4-((4-(carboxymethyl) cyclohexyl) thio) 1-((6 (-chloro 1,3-benzodioxol-5-yl) methyl) 2-cyclopentyl 1H-imidazole 5-carboxylic acid. M.p.= 171° C.

EXAMPLE 20 trans 3-((4-(carboxymethyl) cyclohexyl) thio) 1-((6-chloro 1,3-benzodioxol-5-yl) methyl) 2-(2-thienyl) 1H-imidazole 5-carboxylic acid. M.p.=195° C.

EXAMPLE 21 trans (3-((4-(carboxymethyl) cyclohexyl) thio) 1-((6-chloro 1,3-benzodioxol-5-yl) methyl) 2-cyclohexyl 1H-imidazole 5-carboxylic acid. M.p.= 165° C.

The operation is carried out as in Example 17 using ethyl 4-bromo cyclohexyl carboxylate as in Example 13 instead of the iodated derivative in order to obtain the product of Example 22.

EXAMPLE 22

4-((4-(carboxycyclohexyl) thio) 1-((6-chloro 1,3-benzodioxol-5-yl) methyl 2-(2-furanyl) 1H-imidazole 5-carboxylic acid (cis/trans). M.p.=165° C.

EXAMPLE 23

Disodium salt of 4-((4-(carboxymethyl) cyclohexyl) thio) 1-((6-chloro 1,3-benzodioxol-5-yl) methyl) 2-propyl 1H-imidazole 5-carboxylic acid (cis).

1 g of 4-((4-(carboxymethyl) cyclohexyl) thio) 1-((6-chloro 1,3-benzodioxol-5-yl) methyl) 2-propyl 1H-imidazole 5-carboxylic acid prepared as in Example 10 is recrystallized from ethanol and 780 mg of the pure cis derivative is collected which is dissolved in 31.51 ml of 0.1N soda. The solvents are evaporated off under reduced pressure and 949 mg of the expected cis sodium disalt is collected. M.p.=166° C.

EXAMPLE 24

Dipotassium salt of 4-((4-(carboxymethyl) cyclohexyl) thio) 1-((6-chloro 1,3-benzodioxol-5-yl) methyl) 2-propyl 1H-imidazole 5-carboxylic acid.

The operation is carried out as indicated in Example 23 replacing the 0.1N soda with 0.1N potash. The expected potassium disalt is obtained. M.p. >250° C.

EXAMPLE 29

Pharmaceutical Composition

Tablets were prepared corresponding to the following formula:
Product of Example 2 . . . 50 mg Excipient for a tablet made up to . . . 200 mg (detail of excipient: lactose, talc, starch, magnesium stearate).

PHARMACOLOGICAL RESULTS

1) Study of the Affinity for the Endothelin a Receptor

A membrane preparation is prepared from the heart (ventricles) of a rat. The tissue is ground up in a POLYTRON in a 50 mM Tris buffer pH=7.4.

After 30 minutes at 25° C. (W.B.) the homogenate is centrifuged at 30,000 g for 15 minutes (2 centrifugations with intermediate take-up in the Tris buffer pH 7.4).

The pellets are suspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquoted fractions are distributed in hemolysis tubes and $^{125}$I endothelin (approx. 5,000 dpm/tube) and the product to be studied are added. (The product is first tested at 3×10 5M three times). When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined.

The non-specific bond is determined by the addition of endothelin at $10^{-6}$ M (three times). After incubation at 25° C. for 60 minutes, replacing in a water bath at 0° C. for 5 minutes, filtration under reduced pressure and rinsing with Tris buffer pH 7.4, the radioactivity is counted in the presence of scintillating Triton.

The result is expressed directly as the 50% inhibitory concentration ($IC_{50}$), that is to say as the concentration of product studied, expressed in nM, necessary to displace 50% of the specific radioactivity fixed to the receptor studied.
Result:

The $IC_{50}$'s found for the products of the examples are given in Table 1 hereafter, in nanomoles.

TABLE I

| Product of examples | Endothelin A receptor $IC_{50}$ in nanomoles |
| --- | --- |
| 2 | 1.1 |
| 6 | 1.2 |
| 8 | 1.9 |
| 10 | 1.2 |
| 12 | 1.1 |

2) Study of the Affinity for the Endothelin B Receptor

A membrane preparation is prepared from the rear cortex plus the cerebellum of a rat. The tissue is ground up in a POLYTRON in a 50 mM Tris buffer pH=7.4.

After 30 minutes at 25° C. (W.B.) the homogenate is centrifuged at 30,000 g for 15 minutes (2 centrifugations with intermediate take-up in the Tris buffer pH 7.4).

The pellets are suspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquoted fractions are distributed in hemolysis tubes and $^{125}$I endothelin (approx. 5,000 dpm/tube) and the product to be studied are added. (The product is first tested at $3 \times 10^{-5}$M three times). When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined.

The non-specific bond is determined by the addition of endothelin at $10^{-6}$ M (three times). After incubation at 25° C. for 60 minutes, replacing in a water bath at 0° C. for 5 minutes, filtration under reduced pressure and rinsing with Tris buffer pH 7.4, the radioactivity is counted in the presence of scintillating Triton.

The result is expressed directly as the 50% inhibitory concentration ($IC_{50}$), that is to say as the concentration of product studied, expressed in nM, necessary to displace 50% of the specific radioactivity fixed to the receptor studied.
Results:

The $IC_{50}$'s found for the products of the examples are given in Table I hereafter, in nanomoles.

TABLE I

| Product of examples | Endothelin B receptor $IC_{50}$ in nanomoles |
| --- | --- |
| 2 | 194 |
| 6 | 293 |
| 8 | 600 |
| 10 | 210 |

3) Test for Antagonistic Activity of Endothelin in the Demedullated Rat

Male Sprague Dawley rats (250 to 350 g) are anaesthetized (sodium pentobarbital 60 mg/kg injected by intraperitoneal route). The animal is placed under assisted respiration and a bilateral section of the vagus nerves is carried out. The rat is then demedullated.

The average arterial pressure is recorded with a heparin catheter (PE50) introduced into the carotid of the animal, and connected via a pressure sensor and an amplifier to a recorder (Gould, Pressure Processor). A catheter is introduced into the pudendal vein in order to allow injection of the molecules to be studied. After a stabilization period (about 15 minutes), the product or the solvent is injected 10 minutes before a range of increasing doses of endothelin which are injected every 2 minutes (0.1–0.3–1–3–10 µg/kg).

The anatagonistic activity of the products is estimated by the percentage inhibition in the increase in pressure induced by the endothelin at doses of 3 and 10 µg/kg.

| | | Results | |
| --- | --- | --- | --- |
| | | % inhibition of vasoconstriction | |
| EXAMPLES | Doses mg/kg | $ET_1$ µg/kg | $ET_1$ µg/kg |
| 2 | 0.3 | −56 | −39 |
| | 1.0 | −60 | −65 |
| | 3.0 | −63 | −77 |
| 3 | 1.0 | −52 | −53 |
| | 3.0 | −64 | −71 |
| 4 | 10.0 | −49 | −38 |
| 6 | 1.0 | −42 | −33 |
| | 3.0 | −49 | −37 |
| 8 | 1.0 | −40 | −22 |
| | 3.0 | −57 | −47 |
| 10 | 1.0 | −59 | −39 |
| | 3.0 | −58 | −61 |
| 12 | 10.0 | −30 | −35 |

4) Revealing the Antagonistic Activity of Endothelin, on the Isolated Aorta of a Rat The thoracic aorta is removed from Wistar male rats (approximately 350 g) (IFFA CREDO France) anaesthetized with pentobarbital (60 mg/kg IP) then exsanguinated. The aorta is rapidly put into a physiological solution at ambient temperature. A 1 to 2 mm ring without endothelium is put in an isolated organ bath containing 5 ml of the following physiological solution (composition in mM NaCl: 118.4;

KCl: 4.7; MgSO$_4$, 7H$_2$O: 1.2; CaCl$_2$, 2H$_2$O: 2.5; KH$_2$PO$_4$: 1.2; NaHCO$_3$: 25; glucose: 10.1) the medium is maintained at 37° C. and oxygenated with a mixture of oxygen (95%) carbon dioxide (5%). The initial pressure imposed is 2 g, the rings are left at rest for 60 to 90 minutes. The reference contraction is caused by the addition of 2 successive concentrations of 3 μM of noradrenalin, left in contact for 15 minutes, followed by 3 washings, the second response serves as the reference contraction. After return to the base line, incubation is carried out for 15 minutes with a concentration of the product to be tested or the solvent then cumulative concentrations of endothelin are added every 5 minutes (concentrations of 1 to 1000 μM). The inhibition induced by the product is calculated as a % of the reduction relative to the reactivity of the control curves over 2 points: concentration of 10 and 30 nM of endothelin.

| | Results | |
|---|---|---|
| | Concentration of antagonist | % inhibition of contraction |
| EXAMPLES | μM | ET 10 Nm | ET 30 nM |
| 2 | 0.1 | −71 | −61 |
| | 1.0 | −94 | −100 |
| 6 | 0.1 | −96 | −99 |
| | 1.0 | −96 | −98 |
| 8 | 0.1 | −97 | −97 |
| | 1.0 | −95 | −96 |
| 12 | 0.1 | −88 | −65 |
| | 1.0 | −98 | −98 |

5) Protection Against Sudden Death Induced by IV Injection of Endothelin (ET1) in a Female Mouse A lethal dose of ET1 (10 nmole/kg IV) is injected into female mice. The solvent or the molecules to be studied are injected 10 minutes before (i.v. route) or 30 minutes before (oral route) the endothelin.

The protection is calculated in the form of ED$_{50}$ (50% effective dose, or the dose capable of reducing the mortality by 50% relative to the control group).

| | Results | |
|---|---|---|
| | ED$_{50}$ mg/kg | |
| EXAMPLES | IV | PO |
| 2 | 0.8 | 1.1 |
| 3 | 5.0 | 24.1 |
| 6 | 3.9 | NT |
| 8 | 3.5 | NT |
| 10 | 3.3 | 3.2 |

NT means "not tested"

We claim:

1. A compound selected from the group consisting of all possible racemic, enantiomeric and diastereoisomeric isomer forms of a compound of the formula

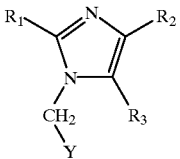

wherein R$_1$ is selected from the group consisting of a) alkyl of 1 to 6 carbon atoms unsubstituted or substituted with at least one hydroxy or alkoxy of 1 to 6 carbon atoms and b) saturated or unsaturated cycloalkyl of 3 to 7 ring members selected from the group consisting of carbon, oxygen, nitrogen and sulfur, R$_2$ and R$_3$ are individually an acid or acid isoteric group, Y is phenyl substituted with dioxol and optionally substituted with a member selected from the group consisting of halogen and alkyl and alkoxy of 1 to 4 carbon atoms and its salts with non-toxic, pharmaceutically acceptable acids or bases.

2. A compound of claim 1 wherein R$_2$ and R$_3$ are individually selected from the group consisting of free carboxy, salified carboxy, carboxy esterified with an alcohol of up to 6 carbon atoms, tetrazolyl and salified tetrazolyl.

3. A compound of claim 1 wherein R$_1$ is selected from the group consisting of a) alkyl of 1 to 6 carbon atoms unsubstituted or substituted with at least one hydroxy or alkoxy of 1 to 6 carbon atoms, b) cycloalkyl of 3 to 6 carbon atoms optionally containing one or two ring members selected from the group consisting of oxygen, nitrogen and sulfur and c) thienyl or furyl, R$_2$ is —(CH$_2$)$_n$—S—A, n is an integer from 0 to 4, A is a) alkyl of 1 to 10 carbon atoms substituted with a member selected from the group consisting of free carboxy, salified carboxy, carboxy esterified with an alcohol of up to 6 carbon atoms, tetrazolyl and salified tetrazolyl, and b) cycloalkyl of 5 to 6 ring members optionally containing 1 or 2 oxygen or nitrogen ring members and optionally substituted by a member selected from,the group consisting of free carboxy, salified carboxy, carboxy esterif ied with an alcohol of up to 6 carbon atoms, tetrazolyl, salified tetrazolyl and alkyl, alkenyl, alkoxy and alkylthio of up to 6 carbon atoms optionally interrupted by oxygen or sulfur and optionally substituted with a member selected from the group consisting of carboxy, salified carboxy, esterified carboxy, tetrazolyl and salified tetrazolyl and R$_3$ is selected from the group consisting of free carboxy, salified carboxy, carboxy esterified with an alcohol of up to 6 carbon atoms, tetrazolyl and salified tetrazolyl.

4. A compound of claim 1 wherein R$_1$ is selected from the group consisting of methoxy methyl, ethyl, n-propyl, isopropyl, n-butyl, isobutyl, tert.-butyl, cyclopentyl, cyclohexyl, dioxolane, dioxane, dithiolane, thienyl and furyl, R$_2$ is selected from the group consisting of a) alkylthio of 3 to 10 carbon atoms substituted with a member selected from the group consisting of free carboxy, salified carboxy, carboxy esterified with an alcohol of up to 6 carbon atoms, tetrazolyl and salified tetrazolyl, cyclohexylthio optionally substituted by carboxy or by alkoxy itself optionally substituted by carboxy and b) cyclohexythio, cyclopentylthio and piperidinylthio substituted with a member selected from the group consisting of free carboxy, salified carboxy, carboxy esterified with an alcohol of up to 6 carbon atoms, tetrazolyl, salified tetrazolyl and alkyl, alkenyl, alkoxy and alkylthio of up to 4 carbon atoms substituted by a member selected from the group consisting of free carboxy, salified carboxy, esterified carboxy, tetrazolyl, salified tetrazolyl, R$_3$ is selected from the group consisting of free carboxy, salified carboxy, carboxy esterified with an alcohol of up to 6 carbon atoms, tetrazolyl and salified tetrazolyl and Y is phenyl substituted with dioxol and optionally by halogen.

5. A compound of claim 1 wherein $R_1$, is selected from the group consisting of methoxy methyl, n-propyl, isopropyl, N-butyl, isobutyl, tert.-butyl and dioxolane, $R_2$ is selected from the group consisting of a) alkylthio of 3 to 5 carbon atoms substituted with a member selected from the group consisting of free carboxy, salified carboxy and carboxy esterified with an alcohol of up to 6 carbon atoms, and b) cyclohexylthio substituted with a member selected from the group consisting of free carboxy, salified carboxy, carboxy esterified with an alcohol of up to 6 carbon atoms and alkyl and alkenyl of up to 4 carbon atoms substituted with a member selected from the group consisting of free carboxy, salified carboxy and carboxy esterified with an alcohol of up to 6 carbon atoms, $R_3$ is selected from the group consisting of free carboxy, salified carboxy and carboxy esterified with an alcohol of up to 6 carbon atoms and Y is phenyl substituted with dioxol and halogen.

6. A compound of claim 1 selected from the group consisting of

- 4-((4-(carboxymethylene) cyclohexyl) thio)-1-((6-chloro-1,3-benzodioxol-5-yl) methyl)-2-propyl-1H-imidazole-5-carboxylic acid,
- 4-((5-carboxypentyl) thio)-1-((6-chloro-1,3-benzodioxol-5-yl) methyl)-2-(1,3-dioxolan-2-yl)-1H-imidazole-5-carboxylic acid,
- 4-((4-(carboxymethyl) cyclohexyl) thio)-1-((6-chloro-1,3-benzodioxol-5-yl) methyl)-2-propyl-1H-imidazole-5-carboxylic acid,
- 1-((6-chloro 1,3-benzodioxol-5-yl) methyl) 4-((4-carboxy-cyclohexyl) thio) 2-propyl 1H-imidazole 5-carboxylic acid,
- 4-(((4-carboxycyclohexyl) methyl) thio) 1-((6-chloro 1,3-benzodioxol-5-yl) methyl) 2-propyl 1H-imidazole 5-carboxylic acid,
- cis 4-(((2-((carboxymethoxy) methyl) cyclohexyl) methyl) thio) 1-((6-chloro 1,3-benzodioxol-5-yl) methyl) 2-propyl 1H-imidazole 5-carboxylic acid,
- trans 4-((4-(carboxymethyl) cyclohexyl) thio) 1-((6-chloro 1,3-benzodioxol-5-yl) methyl) 2-(1,3-dioxolan-2-yl) 1H-imidazole 5-carboxylic acid,
- 4-((4-(carboxymethyl) cyclohexyl) thio) 1-((6-chloro 1,3-benzodioxol-5-yl) methyl) 2-(2-furanyl) 1H-imidazole 5-carboxylic acid,
- trans 4-((4-(carboxymethyl) cyclohexyl) thio) 1-((6-chloro 1,3-benzodioxol-5-yl) methyl) 2-cyclopentyl 1H-imidazole 5-carboxylic acid,
- trans 3-((4-(carboxymethyl) cyclohexyl) thio) 1-((6-chloro 1,3-benzodioxol-5-yl) methyl) 2-(2-thienyl) 1H-imidazole 5-carboxylic acid,
- 4-((4-carboxycyclohexyl) thio) 1-((6-chloro 1,3-benzodioxol-5-yl) methyl) 2-(2-furanyl) 1H-imidazole 5-carboxylic acid,
- disodium salt of 4-((4-(carboxymethyl) cyclohexyl) thio) 1-((6-chloro 1,3-benzodioxol-5-yl) methyl) 2-propyl 1H-imidazole 5-carboxylic acid,
- dipotassium salt of 4-((4-(carboxymethyl) cyclohexyl) thio) 1-((6-chloro 1,3-benzodioxol-5-yl) methyl) 2-propyl 1H-imidazole 5-carboxylic acid.

7. A method of treatment of illness from an abnormal stimulation of endothelin receptors in warm-blooded animals comprising administering to such warm-blooded animals an effective amount of a compound of claim 1 sufficient to treat illnesses due to an abnormal stimulation of endothelin receptors.

* * * * *